United States Patent
Jenney et al.

(10) Patent No.: US 12,296,172 B2
(45) Date of Patent: May 13, 2025

(54) ELECTRODE LEADS HAVING NERVE CONTACT ELEMENTS WITH COIL CONTACTS AND ASSOCIATED SYSTEMS AND METHODS

(71) Applicant: The Alfred E. Mann Foundation for Scientific Research, Valencia, CA (US)

(72) Inventors: Christopher Reed Jenney, Valencia, CA (US); Timothy Strickland, La Crescenta, CA (US)

(73) Assignee: The Alfred E. Mann Foundation for Scientific Research, Valencia, CA (US)

( * ) Notice: Subject to any disclaimer, the term of this patent is extended or adjusted under 35 U.S.C. 154(b) by 404 days.

(21) Appl. No.: 17/710,570

(22) Filed: Mar. 31, 2022

(65) Prior Publication Data
US 2023/0241394 A1 Aug. 3, 2023

Related U.S. Application Data

(60) Provisional application No. 63/305,443, filed on Feb. 1, 2022.

(51) Int. Cl.
*A61N 1/36* (2006.01)
*A61N 1/05* (2006.01)

(52) U.S. Cl.
CPC ....... *A61N 1/36125* (2013.01); *A61N 1/0556* (2013.01); *A61N 1/3606* (2013.01)

(58) Field of Classification Search
CPC . A61N 1/36125; A61N 1/0556; A61N 1/3606
USPC ....................................................... 607/118
See application file for complete search history.

(56) References Cited

U.S. PATENT DOCUMENTS

| | | |
|---|---|---|
| 4,573,481 A | 3/1986 | Bullara |
| 4,602,624 A | 7/1986 | Naples et al. |
| 4,940,065 A | 7/1990 | Tanagho et al. |
| 5,251,634 A | 10/1993 | Weinberg |
| 5,400,784 A | 3/1995 | Durand et al. |
| 5,439,485 A | 8/1995 | Mar et al. |
| 5,487,756 A | 1/1996 | Kallesoe et al. |
| 5,634,462 A | 6/1997 | Tyler et al. |

(Continued)

FOREIGN PATENT DOCUMENTS

| | | |
|---|---|---|
| CN | 112402786 A | 2/2021 |
| WO | WO 2008092246 A1 | 8/2008 |

(Continued)

OTHER PUBLICATIONS

PCT International Search and Written Opinion dated Oct. 7, 2022 for PCT App. Ser. No. PCT/US2022/022877.

(Continued)

*Primary Examiner* — Michael J Lau
(74) *Attorney, Agent, or Firm* — Henricks Slavin LLP

(57) ABSTRACT

An electrode lead including an elongate lead body and a nerve cuff (or other nerve contact element) including an electrically insulative cuff body (or other contact body) affixed to the distal end of the lead body and at least one electrically conductive coil partially embedded in the cuff body (or other contact body) such that there are non-embedded portions, which together define a flexible coil contact that is associated with the front outer surface of the cuff body (or other contact body), and embedded portions.

19 Claims, 15 Drawing Sheets

(56) References Cited

U.S. PATENT DOCUMENTS

| | | | |
|---|---|---|---|
| 5,919,220 A | 7/1999 | Stieglitz et al. | |
| 6,066,165 A | 5/2000 | Racz | |
| 6,093,197 A | 7/2000 | Bakula et al. | |
| 6,210,339 B1 | 4/2001 | Kiepen et al. | |
| 6,292,703 B1* | 9/2001 | Meier | A61B 5/287 |
| | | | 607/118 |
| 7,383,090 B2 | 6/2008 | O'Brien et al. | |
| 7,794,256 B1 | 9/2010 | Sochor | |
| 7,809,442 B2 | 10/2010 | Bolea et al. | |
| 7,996,092 B2* | 8/2011 | Mrva | A61N 1/0556 |
| | | | 607/118 |
| 8,116,882 B2 | 2/2012 | Kowalczewski | |
| 8,155,757 B1 | 4/2012 | Neisz et al. | |
| 8,224,449 B2 | 7/2012 | Carbunaru et al. | |
| 8,311,645 B2 | 11/2012 | Bolea et al. | |
| 8,340,785 B2 | 12/2012 | Bonde et al. | |
| 8,660,665 B2 | 2/2014 | Walter et al. | |
| 8,792,973 B2 | 7/2014 | Moran et al. | |
| 8,934,992 B2 | 1/2015 | Johnson et al. | |
| 9,186,511 B2 | 11/2015 | Bolea | |
| 9,227,053 B2 | 1/2016 | Bonde et al. | |
| 9,486,628 B2 | 11/2016 | Christopherson et al. | |
| 9,549,708 B2 | 1/2017 | Mercanzini et al. | |
| 9,603,538 B2 | 3/2017 | Fisher et al. | |
| 9,849,288 B2 | 12/2017 | Meadows et al. | |
| 9,889,304 B2 | 2/2018 | Mercanzini | |
| 9,931,045 B2 | 4/2018 | Brunnett et al. | |
| 10,758,723 B2 | 9/2020 | Fang et al. | |
| 11,833,348 B2 | 12/2023 | Brandt et al. | |
| 12,194,290 B2 | 1/2025 | Dearden et al. | |
| 2002/0198582 A1 | 12/2002 | Edell et al. | |
| 2005/0070982 A1 | 3/2005 | Heruth et al. | |
| 2005/0186829 A1 | 8/2005 | Balsells | |
| 2006/0004430 A1* | 1/2006 | Rossing | A61N 1/3752 |
| | | | 607/116 |
| 2006/0030919 A1* | 2/2006 | Mrva | A61N 1/0556 |
| | | | 607/118 |
| 2007/0123765 A1 | 5/2007 | Hetke et al. | |
| 2007/0185542 A1* | 8/2007 | Bolea | A61N 1/36114 |
| | | | 607/42 |
| 2008/0082137 A1 | 4/2008 | Kieval et al. | |
| 2008/0103545 A1 | 5/2008 | Bolea et al. | |
| 2008/0172101 A1* | 7/2008 | Bolea | A61N 1/3686 |
| | | | 607/116 |
| 2009/0132042 A1 | 5/2009 | Hetke et al. | |
| 2009/0210042 A1 | 8/2009 | Kowalczewski | |
| 2010/0305674 A1 | 12/2010 | Zarembo et al. | |
| 2010/0331933 A1 | 12/2010 | Carbunaru et al. | |
| 2011/0066196 A1 | 3/2011 | Alexander et al. | |
| 2011/0130815 A1 | 6/2011 | Gibson et al. | |
| 2011/0154655 A1 | 6/2011 | Hetke et al. | |
| 2011/0251473 A1 | 10/2011 | Moran et al. | |
| 2011/0301665 A1 | 12/2011 | Mercanzini et al. | |
| 2012/0089153 A1* | 4/2012 | Christopherson | A61B 5/085 |
| | | | 606/129 |
| 2012/0150255 A1 | 6/2012 | Lindenthaler et al. | |
| 2012/0154256 A1 | 6/2012 | Grover et al. | |
| 2012/0277819 A1 | 11/2012 | Cowley et al. | |
| 2012/0316417 A1 | 12/2012 | Vetter | |
| 2013/0030352 A1 | 1/2013 | Seymour et al. | |
| 2013/0085361 A1 | 4/2013 | Mercanzini et al. | |
| 2013/0090711 A1 | 4/2013 | Ramachandran et al. | |
| 2013/0150938 A1 | 6/2013 | Carbunaru et al. | |
| 2013/0304174 A1 | 11/2013 | Langhals et al. | |
| 2014/0005763 A1 | 1/2014 | Cederna et al. | |
| 2014/0058482 A1 | 2/2014 | Gupta et al. | |
| 2014/0163659 A1 | 6/2014 | Boling | |
| 2014/0188202 A1* | 7/2014 | Zarembo | A61N 1/0556 |
| | | | 607/118 |
| 2014/0228905 A1 | 8/2014 | Bolea | |
| 2014/0303703 A1 | 10/2014 | Mercanzini et al. | |
| 2015/0119673 A1 | 4/2015 | Pellinen et al. | |
| 2015/0128413 A1 | 5/2015 | Vetter et al. | |
| 2015/0157854 A1 | 6/2015 | Hetke et al. | |
| 2015/0174396 A1 | 6/2015 | Fisher et al. | |
| 2015/0224307 A1 | 8/2015 | Bolea | |
| 2015/0374975 A1 | 12/2015 | Callegari et al. | |
| 2016/0184581 A1 | 6/2016 | Bonde et al. | |
| 2016/0199637 A1 | 7/2016 | Xu et al. | |
| 2016/0287863 A1 | 10/2016 | Mercanzini et al. | |
| 2016/0331326 A1 | 11/2016 | Xiang et al. | |
| 2016/0331994 A1 | 11/2016 | Smith et al. | |
| 2017/0225004 A1* | 8/2017 | Casse | A61N 2/02 |
| 2017/0266436 A1 | 9/2017 | Suwito et al. | |
| 2017/0319846 A1 | 11/2017 | Plachta et al. | |
| 2018/0117313 A1 | 5/2018 | Schmidt et al. | |
| 2018/0132790 A1 | 5/2018 | Yao et al. | |
| 2018/0221660 A1 | 8/2018 | Suri et al. | |
| 2018/0318577 A1 | 11/2018 | Ng et al. | |
| 2018/0318578 A1 | 11/2018 | Ng et al. | |
| 2019/0060646 A1 | 2/2019 | Ng et al. | |
| 2019/0069949 A1* | 3/2019 | Vrba | A61B 18/02 |
| 2019/0282805 A1 | 9/2019 | Schmidt et al. | |
| 2020/0069935 A1 | 3/2020 | Johnson et al. | |
| 2020/0083922 A1 | 3/2020 | Hong et al. | |
| 2020/0146583 A1 | 5/2020 | Hestad et al. | |
| 2020/0230412 A1 | 7/2020 | Rondoni et al. | |
| 2020/0230421 A1 | 7/2020 | Zaidi et al. | |
| 2020/0306526 A1* | 10/2020 | Doguet | A61N 1/375 |
| 2021/0085964 A1* | 3/2021 | Zaidi | A61N 1/0556 |
| 2021/0205662 A1 | 7/2021 | Lu et al. | |
| 2022/0062629 A1 | 3/2022 | Dearden | |
| 2022/0088374 A1 | 3/2022 | Ackermann et al. | |
| 2022/0184387 A1 | 6/2022 | Searfoss et al. | |
| 2022/0313987 A1 | 10/2022 | Jenny et al. | |
| 2023/0010510 A1 | 1/2023 | Brandt et al. | |
| 2024/0009452 A1 | 1/2024 | Jenny et al. | |
| 2024/0058602 A1 | 2/2024 | Brandt et al. | |
| 2024/0108883 A1 | 4/2024 | Trivedi et al. | |

FOREIGN PATENT DOCUMENTS

| | | |
|---|---|---|
| WO | WO 2009045772 A1 | 4/2009 |
| WO | WO 2012154256 A1 | 11/2012 |
| WO | WO 2013188871 A1 | 12/2013 |
| WO | WO 2016039768 A1 | 3/2016 |
| WO | WO 2020182293 A1 | 9/2020 |
| WO | WO 2021108810 A1 | 6/2021 |

OTHER PUBLICATIONS

U.S. Appl. No. 17/463,611, filed Sep. 1, 2021, 20220062629 A1.
U.S. Appl. No. 18/968,650, filed Dec. 4, 2024.
U.S. Appl. No. 18/981,465, filed Dec. 14, 2024.
U.S. Appl. No. 17/463,630, filed Sep. 1, 2021 U.S. Pat. No. 11,833,348 B2.
U.S. Appl. No. 18/495,503, filed Oct. 26, 2023, 20240058602 A1.
U.S. Appl. No. 17/683,598, filed Mar. 1, 2022, 20220313987 A1.
U.S. Appl. No. 17/710,570, filed Mar. 31, 2022, 20230241394 A1.
U.S. Appl. No. 18/468,730, filed Sep. 17, 2023, 20240108883 A1.
U.S. Appl. No. 18/186,927, filed Mar. 20, 2023, 20240009452 A1.
U.S. Appl. No. 18/939,479, filed Nov. 6, 2024.

* cited by examiner

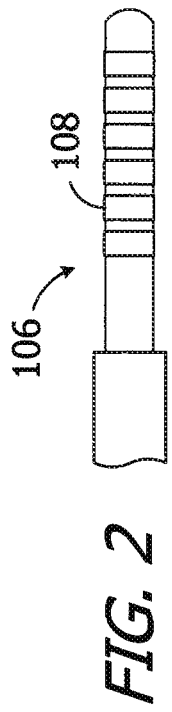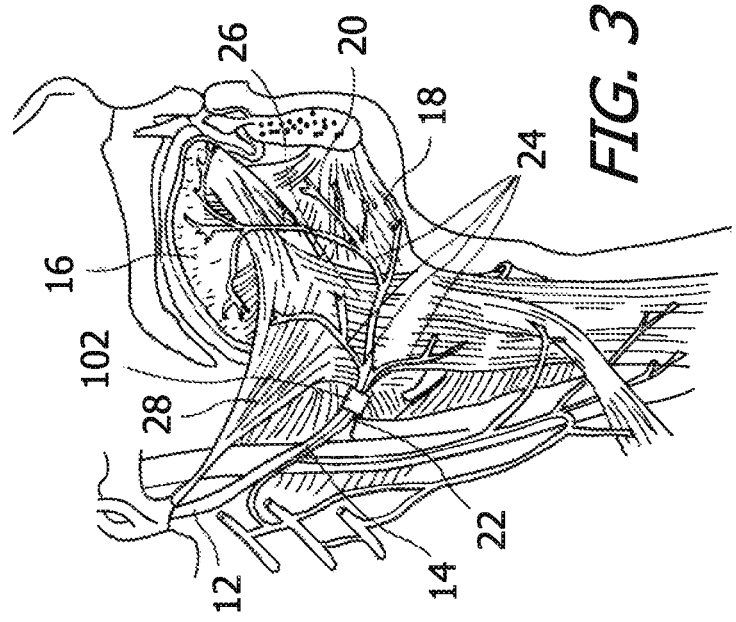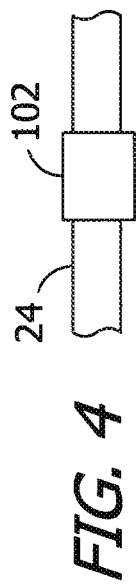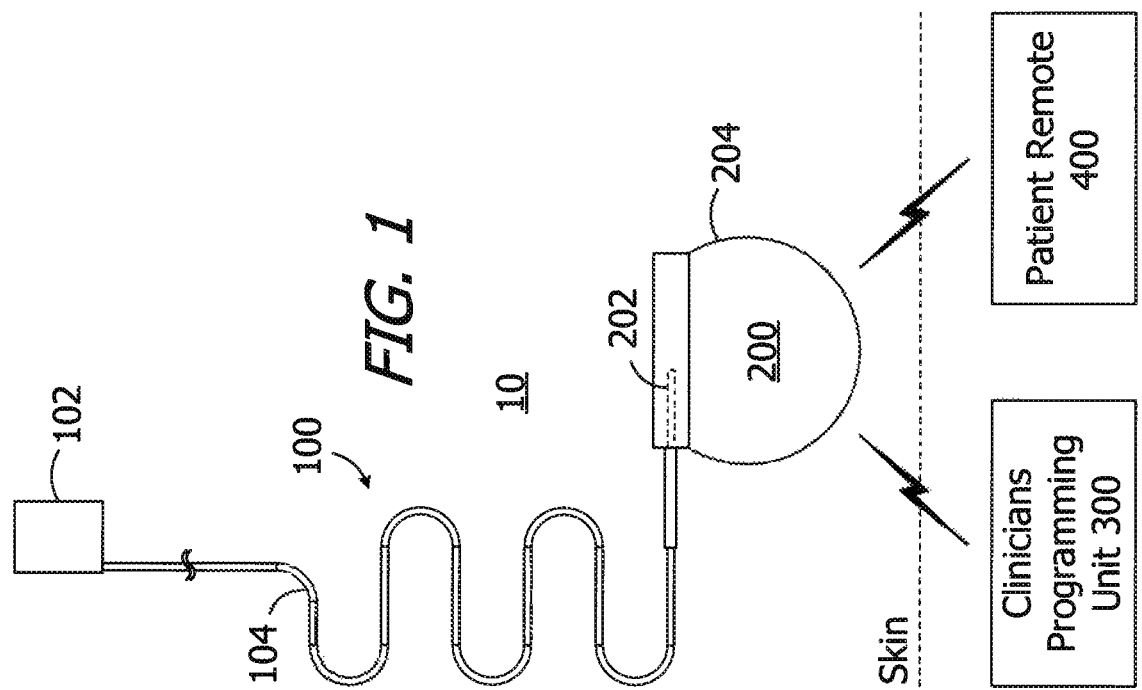

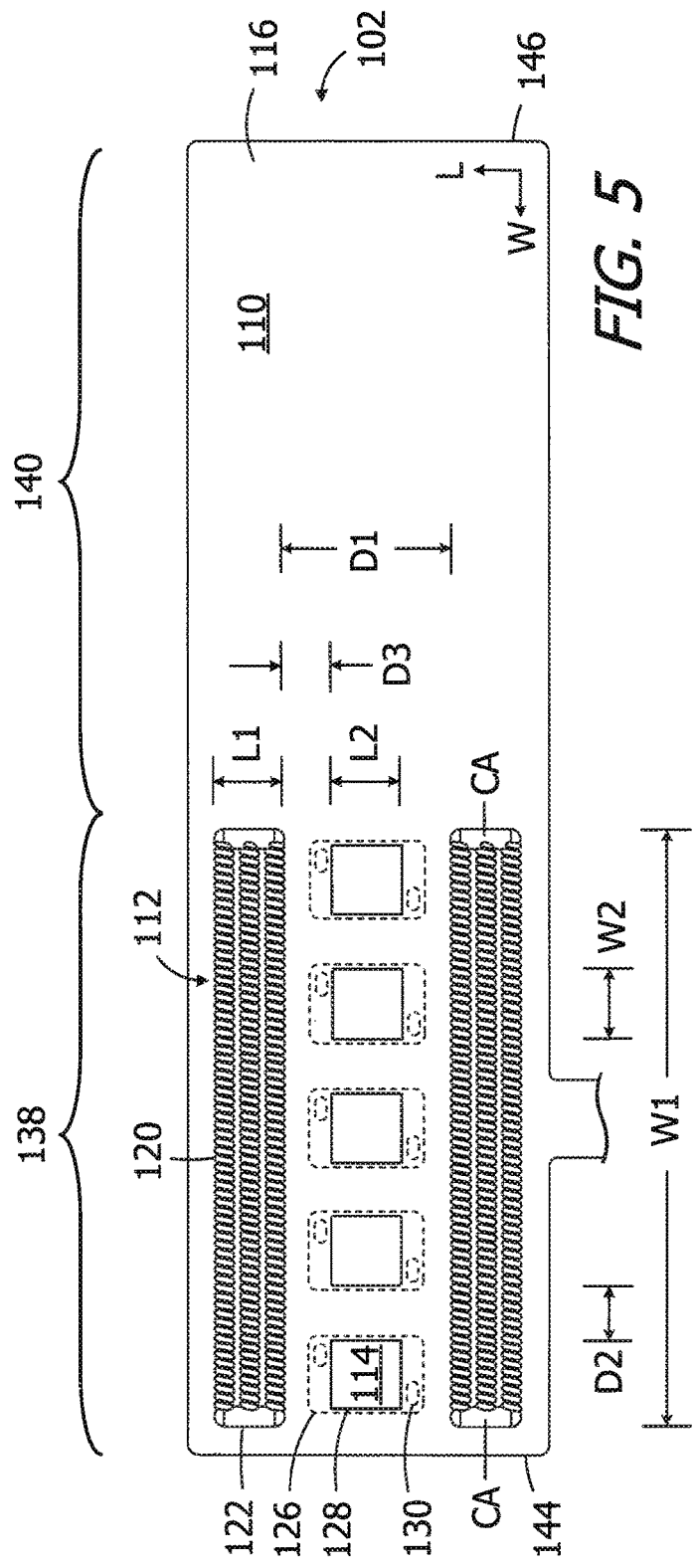
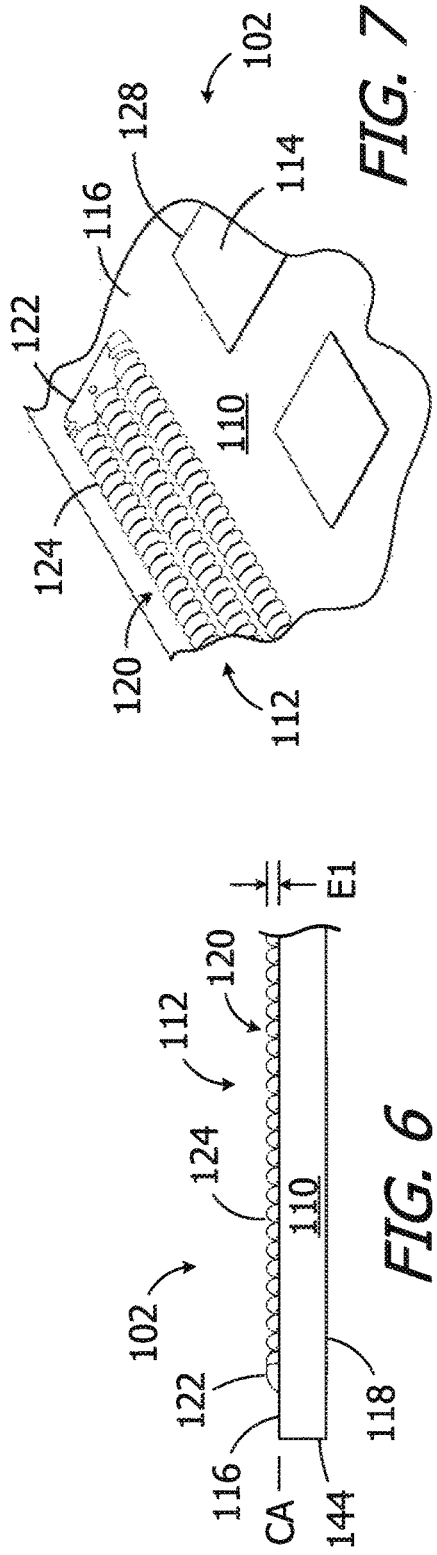

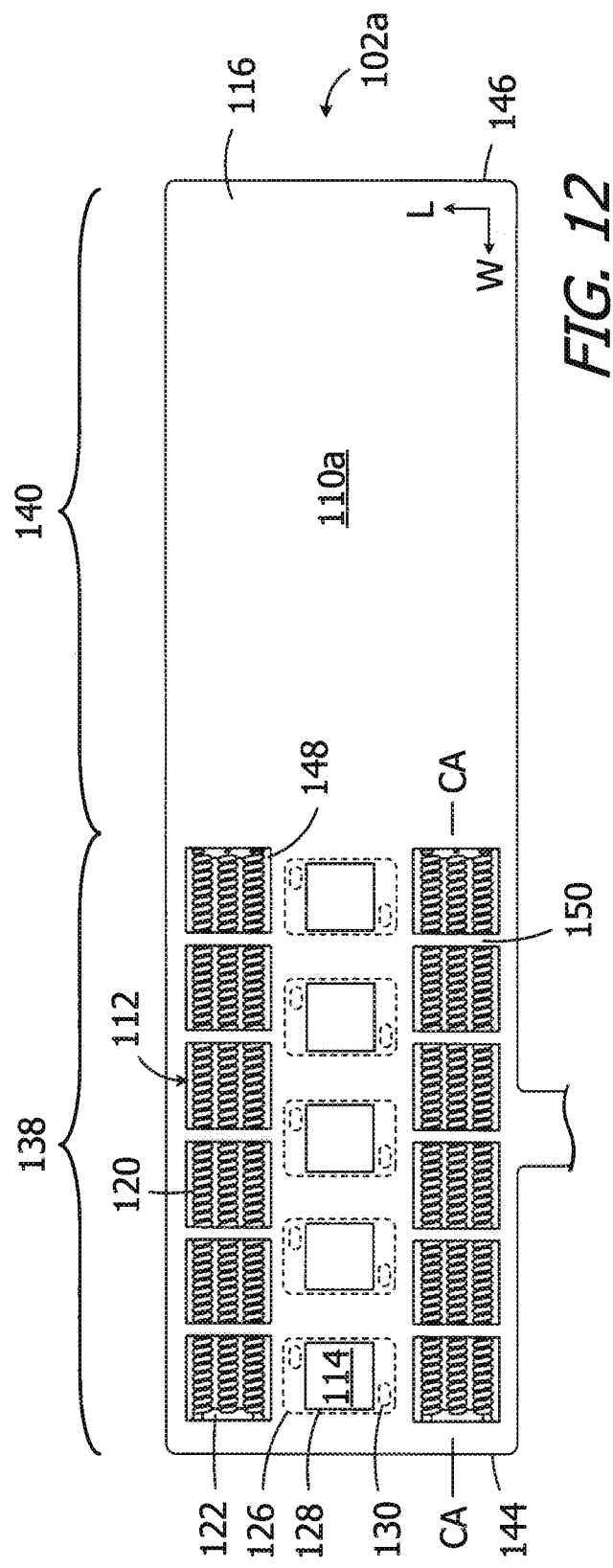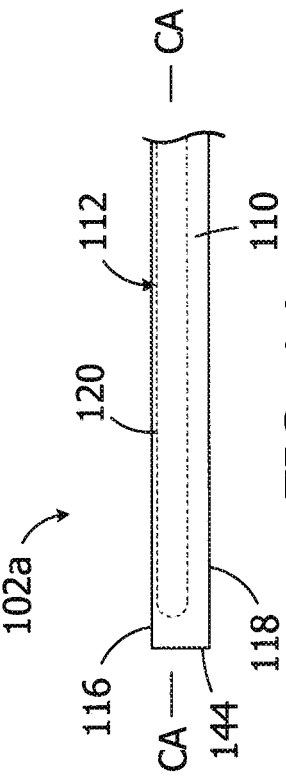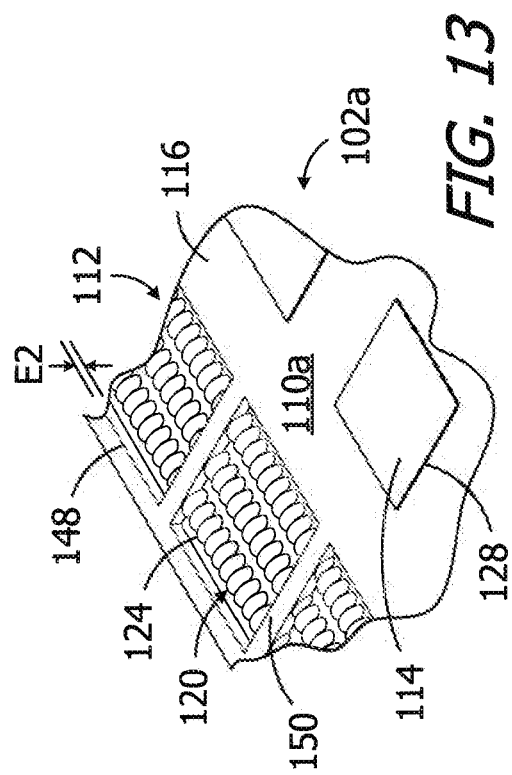

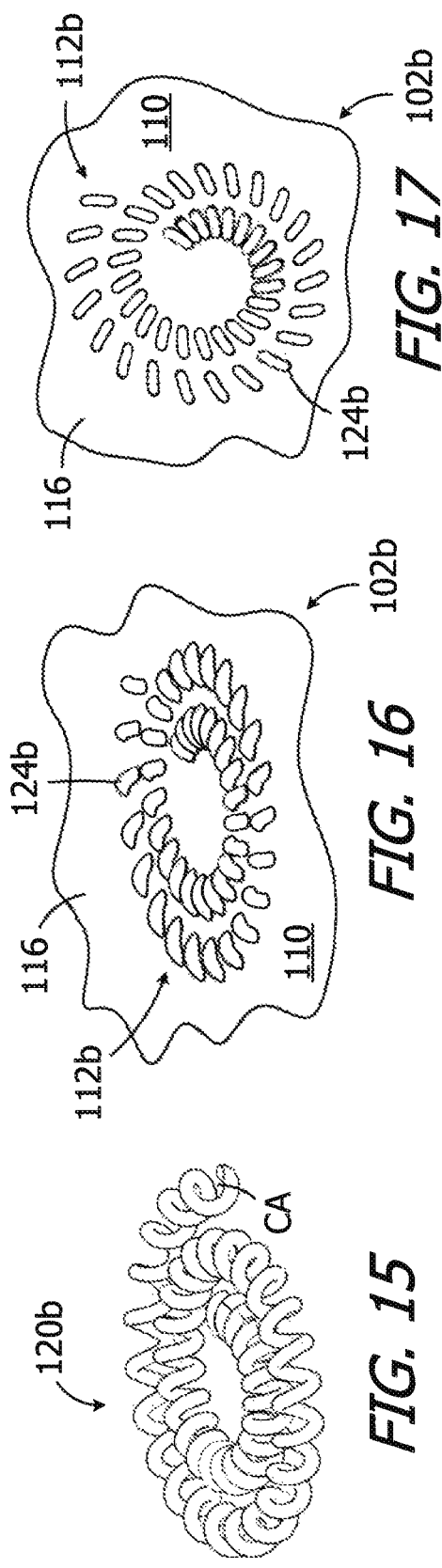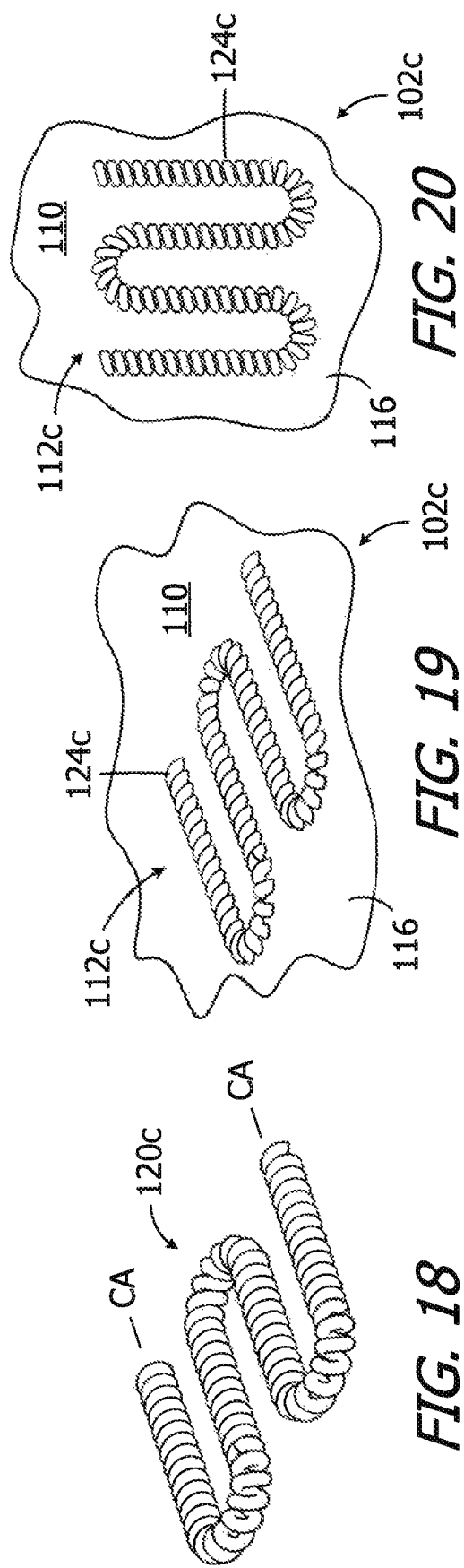

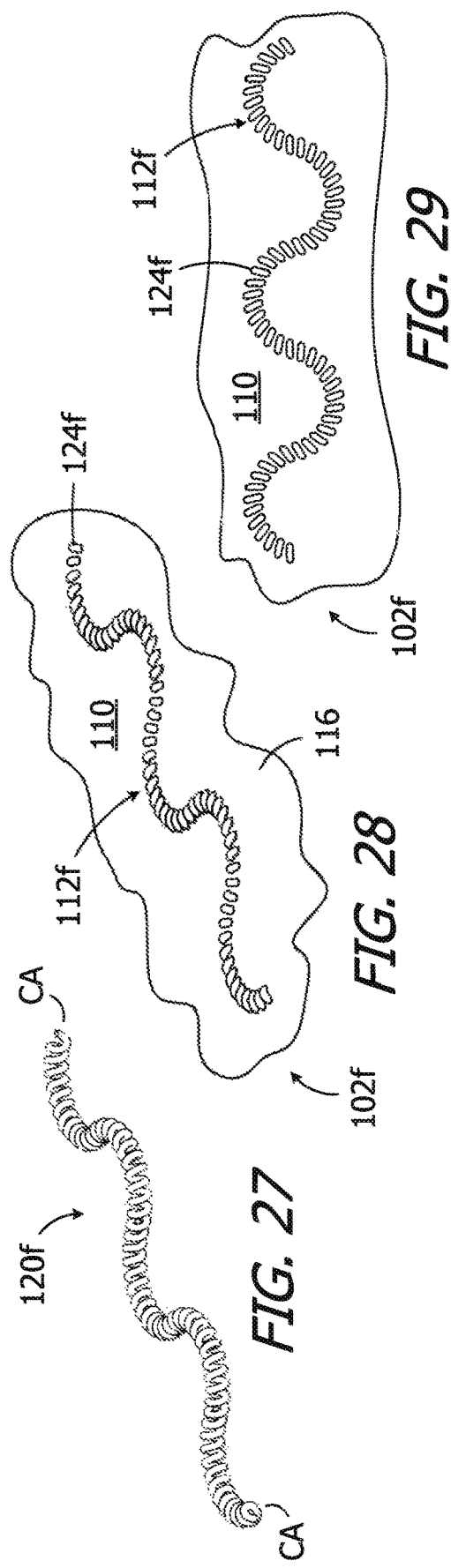

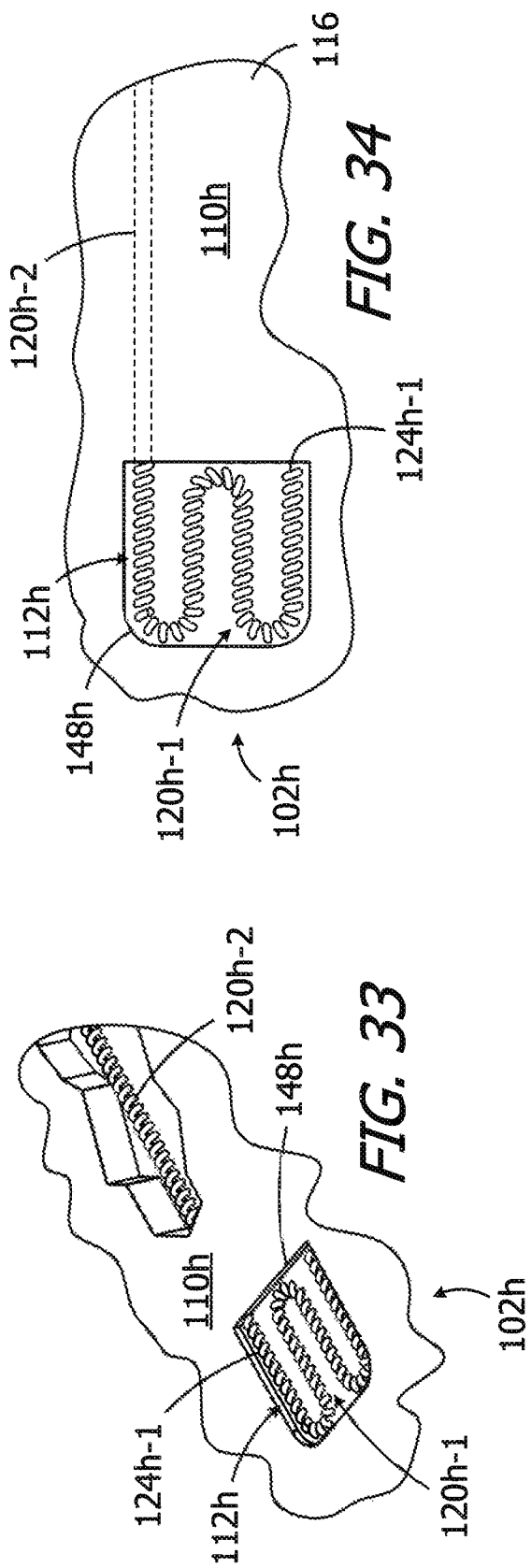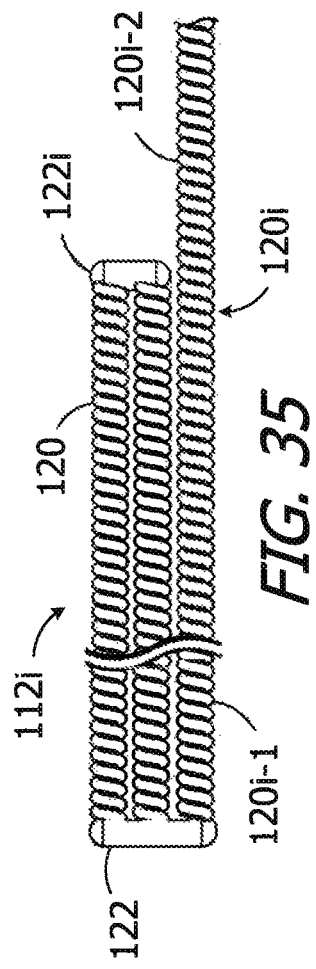

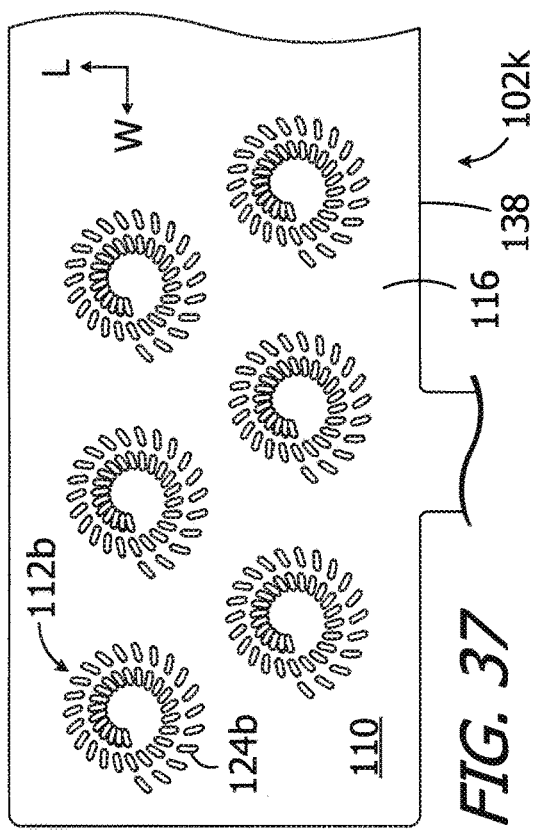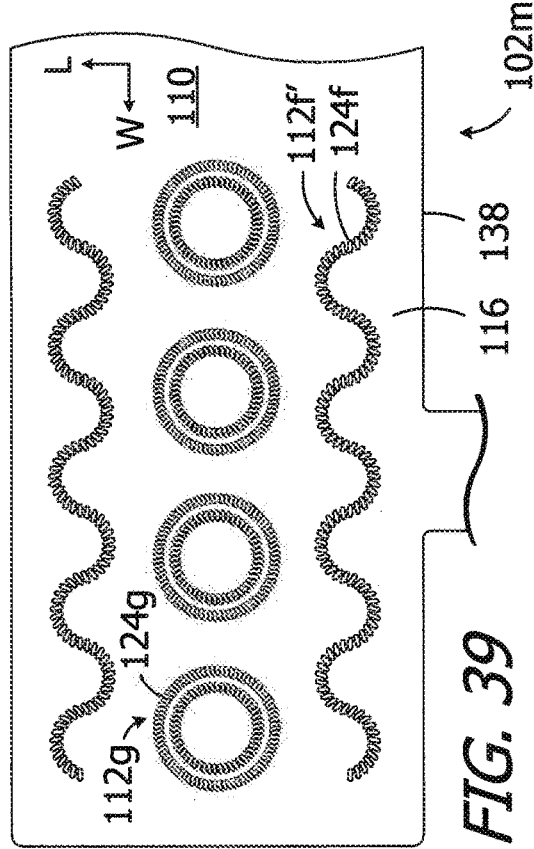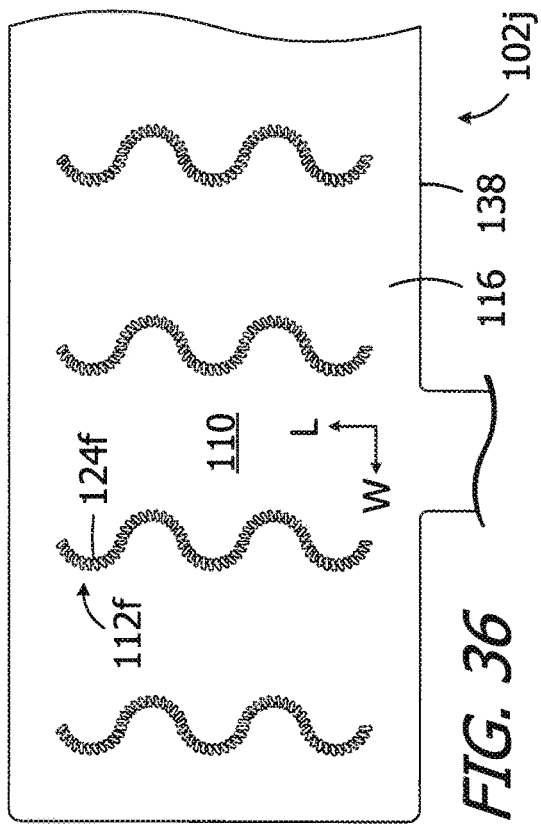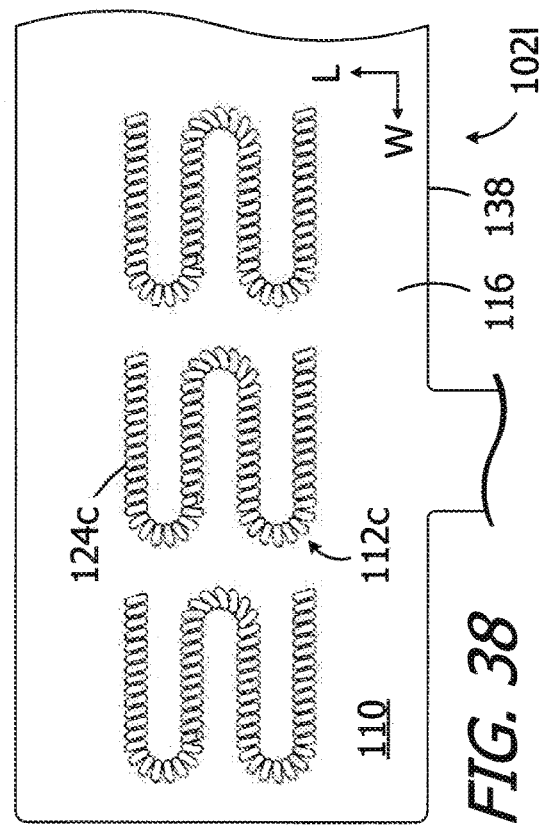

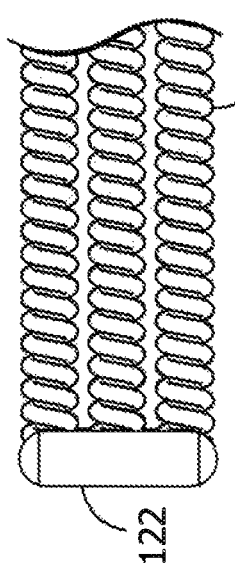
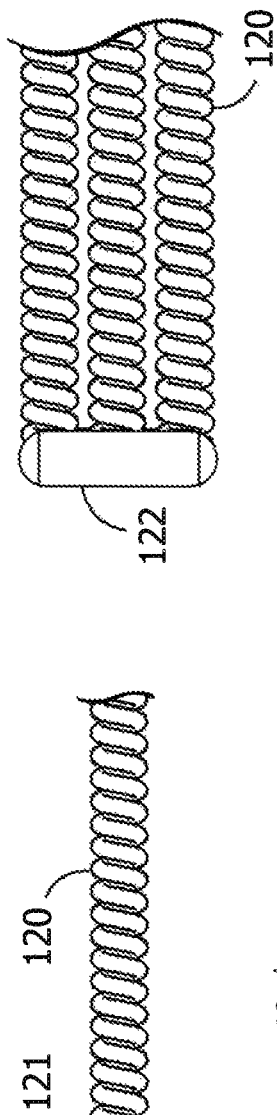
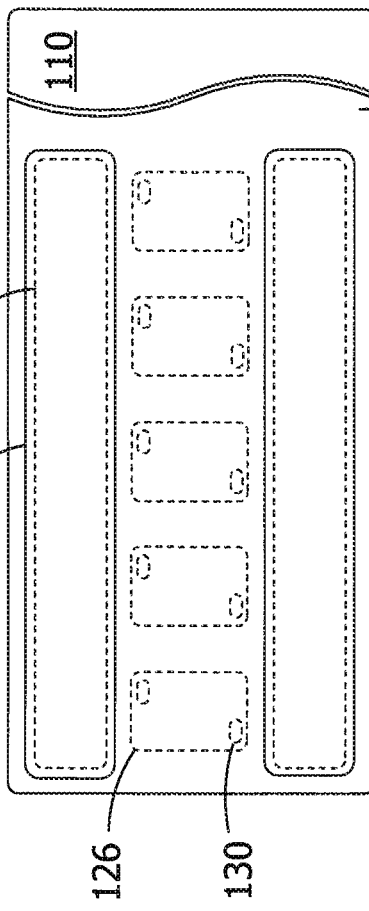
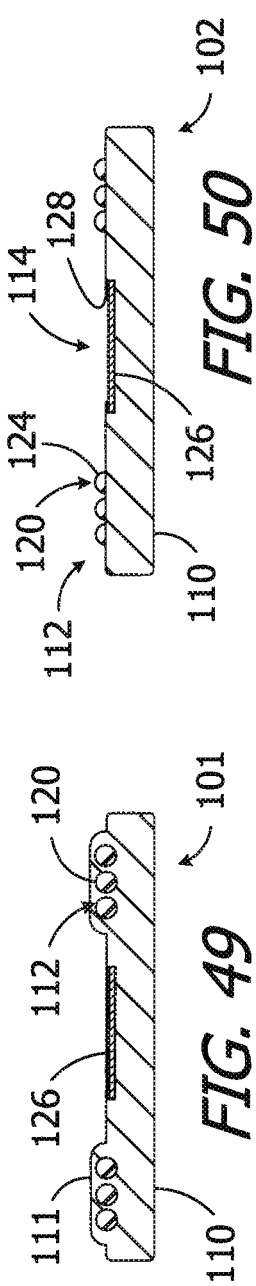

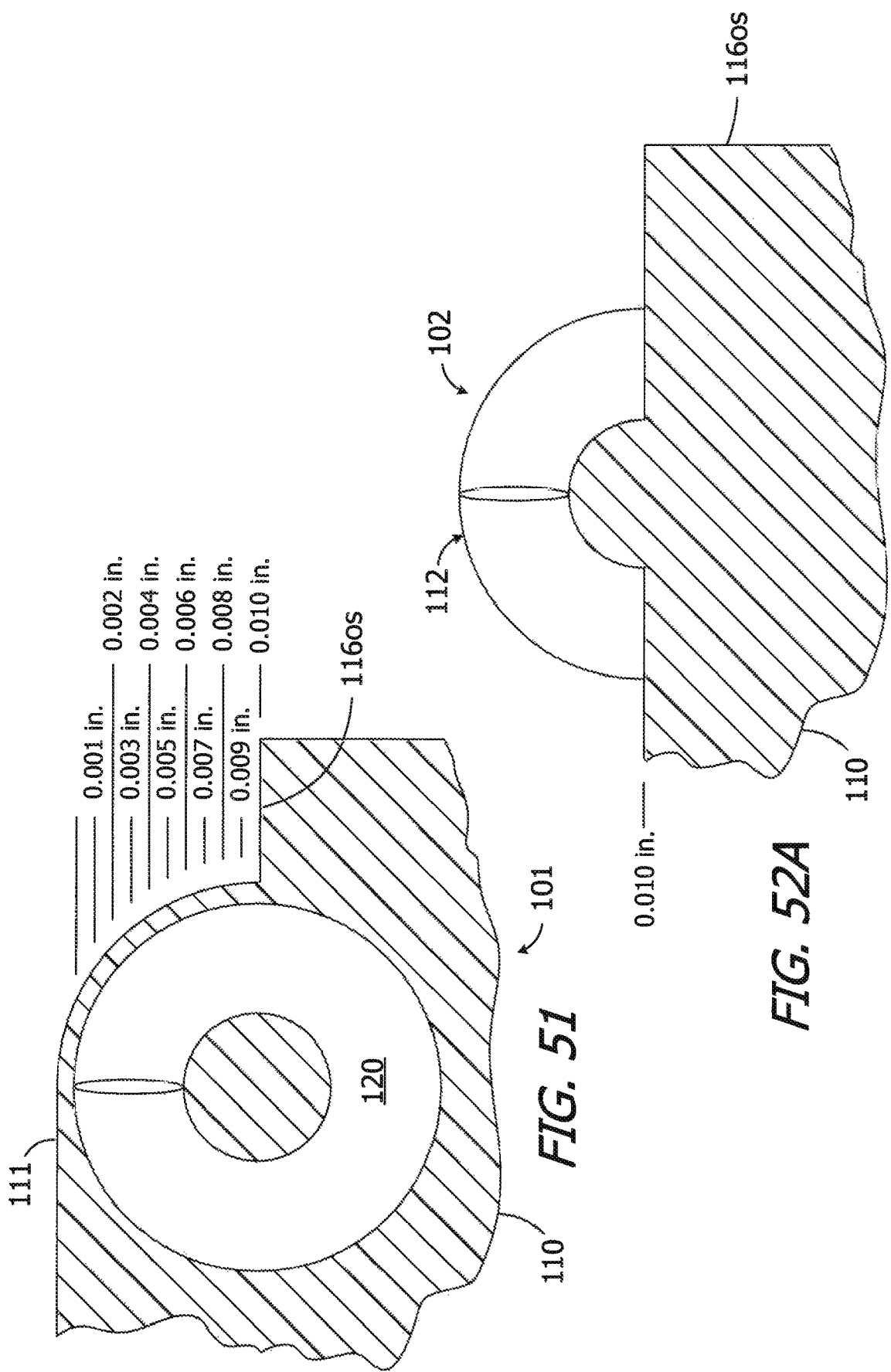

ELECTRODE LEADS HAVING NERVE CONTACT ELEMENTS WITH COIL CONTACTS AND ASSOCIATED SYSTEMS AND METHODS

CROSS-REFERENCE TO RELATED APPLICATION

This application claims the benefit of U.S. Provisional Application No. 63/305,443, filed Feb. 1, 2022, and entitled "Embedded Micro-Coil Cuff Electrodes," which is incorporated herein by reference.

BACKGROUND OF THE INVENTIONS

1. Field of Inventions

The present inventions relate generally to nerve stimulation such as, for example, the treatment of obstructive sleep apnea by stimulating the hypoglossal nerve.

2. Description of the Related Art

Obstructive sleep apnea (OSA) is a highly prevalent sleep disorder that is caused by the collapse of or increase in the resistance of the pharyngeal airway, often resulting from tongue obstruction. The obstruction of the upper airway is mainly caused by reduced genioglossus muscle activity during the deeper states of non-rapid eye movement (NREM) sleep. In some OSA patients, obstruction occurs predominantly during rapid eye movement (REM) sleep. This is known as REM OSA and has different cardiometabolic and neurocognitive risks. Obstruction of the upper airway causes breathing to pause during sleep. Cessation of breathing, in turn, causes a decrease in the blood oxygen saturation level, which is eventually corrected when the person wakes up and resumes breathing. The long-term effects of OSA include, but are not limited to, high blood pressure, heart failure, strokes, diabetes, headaches, and general daytime sleepiness and memory loss.

Some proposed methods of alleviating apneic events involve the use of neurostimulators to open the upper airway. Such therapy involves stimulating the nerve fascicles of the hypoglossal nerve (HGN) that innervate the intrinsic and extrinsic muscles of the tongue in a manner that prevents retraction of the tongue, which would otherwise close the upper airway during the inspiration portion of the respiratory cycle. In some instances, the trunk of the HGN is stimulated with a nerve cuff, including a cuff body and a plurality of flat spaced electrically conductive contacts on the cuff body, that is positioned around the HGN trunk. The HGN trunk nerve cuff may be configured in such a manner that it can be used to selectively stimulate nerve fascicles which innervate muscles that extend the tongue, while avoiding other nerve fascicles, with what is predominantly radial vector stimulation. For example, the contacts may be axially aligned and circumferentially spaced around the perimeter of the HGN trunk. In other instances, a nerve cuff is placed on the branch of the HGN that is responsible for protruding the tongue (hereafter "HGN genioglossus muscle branch" or "HGN GM branch"). A smaller diameter cuff with two or three axially spaced contacts may be used at the HGN GM branch because the nerve fascicles within this branch generally innervate the specific tongue protrusor muscle, but not other muscles. Put another way, the entire HGN GM branch is stimulated with what is predominantly axial vector stimulation. Exemplary nerve cuffs are illustrated and described in U.S. Pat. Pub. Nos. 2018/0318577A1, 2018/0318578A1, 2019/0060646A1 and 2019/0282805, which are incorporated herein by reference in their entirety.

SUMMARY

The present inventor has determined that the contacts on nerve cuffs, nerve paddles, nerve strips and other nerve contact elements are susceptible to improvement. In particular, the present inventors have determined that it would be desirable to provide contacts with more surface area than a flat contact. The present inventors have also determined that it would be desirable to provide contacts with bending properties that are superior to a flat contact.

An electrode lead in accordance with at least one of the present inventions may include an elongate lead body and a nerve cuff including an electrically insulative cuff body affixed to the distal end of the lead body and at least one electrically conductive coil partially embedded in the cuff body such that there are non-embedded portions, which together define a coil contact that is associated with the front outer surface of the cuff body, and embedded portions. The present inventions also include systems with an implantable pulse generator or other implantable stimulation device in combination with such an electrode lead.

An electrode lead in accordance with at least one of the present inventions may include an elongate lead body and a nerve contact element including an electrically insulative contact body affixed to the distal end of the lead body and at least one electrically conductive coil partially embedded in the contact body such that there are non-embedded portions, which together define a coil contact that is associated with the front outer surface of the contact body, and embedded portions. The present inventions also include systems with an implantable pulse generator or other implantable stimulation device in combination with such an electrode lead.

There are a variety of advantages associated with such electrode leads and systems. By way of example, but not limitation, the coil contacts provide superior bending properties, and create larger surface areas, than conventional flat contacts.

BRIEF DESCRIPTION OF THE DRAWINGS

Detailed descriptions of exemplary embodiments will be made with reference to the accompanying drawings.

FIG. 1 is a plan view of a stimulation system in accordance with one embodiment of a present invention.

FIG. 2 is a plan view of a portion of the stimulation system illustrated in FIG. 1.

FIG. 3 is a cut-away anatomical drawing of the head and neck area illustrating the muscles that control movement of the tongue, the HGN and its branches that innervate these muscles, and the nerve cuff illustrated in FIG. 1 on the HGN trunk.

FIG. 4 is a plan view showing the nerve cuff illustrated in FIG. 1 on the HGN GM branch.

FIG. 5 is a front view of the nerve cuff illustrated in FIG. 1 in an unfurled state.

FIG. 6 is a side view of a portion of the nerve cuff illustrated in FIG. 1 in an unfurled state.

FIG. 7 is a perspective view of a portion of the nerve cuff illustrated in FIG. 1 in an unfurled state.

FIG. 12 is a front view of a nerve cuff in accordance with one embodiment of a present invention.

FIG. 13 is a perspective view of a portion of the nerve cuff illustrated in FIG. 12 in an unfurled state.

FIG. 14 is a side view of a portion of the nerve cuff illustrated in FIG. 12 in an unfurled state.

FIG. 15 is a perspective view of a conductive coil in accordance with one embodiment of a present invention.

FIG. 16 is a perspective view of a portion of a nerve cuff in accordance with one embodiment of a present invention.

FIG. 17 is a front view of a portion of the nerve cuff illustrated in FIG. 16.

FIG. 18 is a perspective view of a conductive coil in accordance with one embodiment of a present invention.

FIG. 19 is a perspective view of a portion of a nerve cuff in accordance with one embodiment of a present invention.

FIG. 20 is a front view of a portion of the nerve cuff illustrated in FIG. 19.

FIG. 27 is a perspective view of a conductive coil in accordance with one embodiment of a present invention.

FIG. 28 is a perspective view of a portion of a nerve cuff in accordance with one embodiment of a present invention.

FIG. 29 is a front view of a portion of the nerve cuff illustrated in FIG. 28.

FIG. 30 is a perspective view of conductive coils in accordance with one embodiment of a present invention.

FIG. 31 is a perspective view of a portion of a nerve cuff in accordance with one embodiment of a present invention.

FIG. 32 is a front view of a portion of the nerve cuff illustrated in FIG. 31.

FIG. 33 is a perspective cutaway view of a portion of a nerve cuff in accordance with one embodiment of a present invention.

FIG. 34 is a front view of a portion of the nerve cuff illustrated in FIG. 33.

FIG. 35 is a plan view of conductive coils in accordance with one embodiment of a present invention.

FIG. 36 is a front view of a nerve cuff in accordance with one embodiment of a present invention.

FIG. 37 is a front view of a nerve cuff in accordance with one embodiment of a present invention.

FIG. 38 is a front view of a nerve cuff in accordance with one embodiment of a present invention.

FIG. 39 is a front view of a nerve cuff in accordance with one embodiment of a present invention.

FIG. 46 is a plan view of a portion of a conductive coil in accordance with one embodiment of a present invention.

FIG. 47 is a plan view of portions of conductive coils in accordance with one embodiment of a present invention.

FIG. 48 is a front view of a nerve cuff blank in accordance with one embodiment of a present invention.

FIG. 49 is a section view taken along line 49-49 in FIG. 48.

FIG. 50 is a section view of the nerve cuff illustrated in FIG. 1.

FIG. 51 is a partial section view showing a portion of the nerve cuff blank illustrated in FIG. 49.

FIG. 52A is a partial section view showing a portion of a nerve cuff formed from the blank illustrated in FIG. 49.

DETAILED DESCRIPTION OF THE EXEMPLARY EMBODIMENTS

Figure 8:
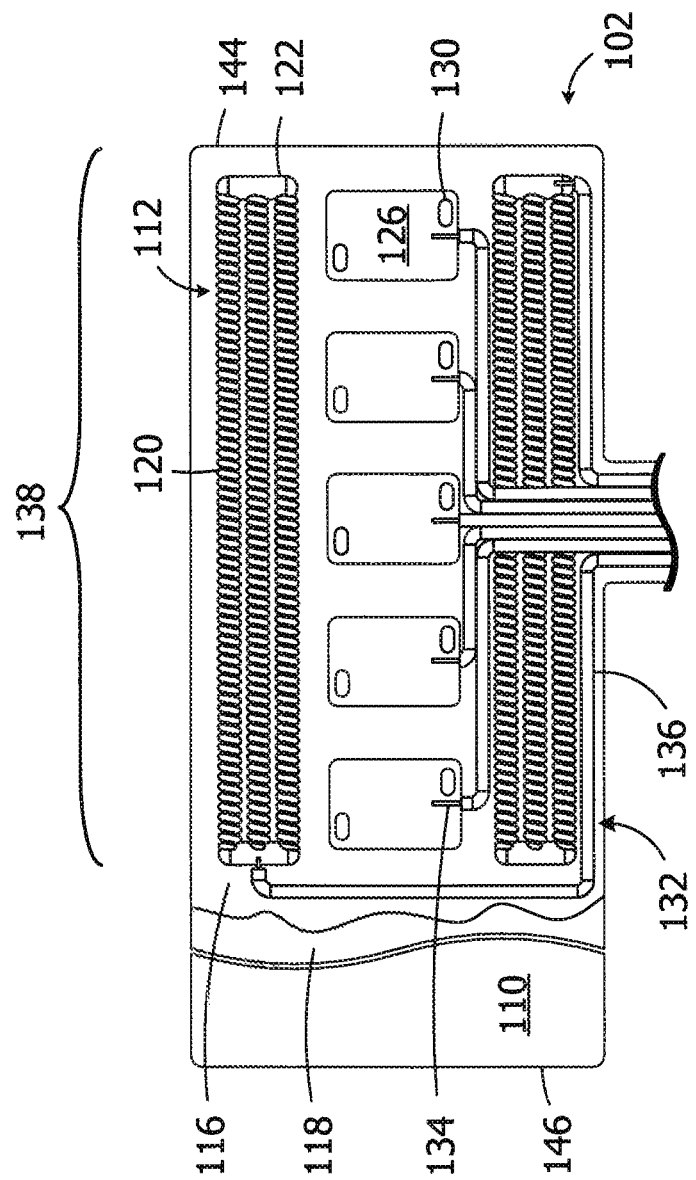
FIG. 8 is a rear, cutaway view of the nerve cuff illustrated in FIG. 1 in an unfurled state.

The following is a detailed description of the best presently known modes of carrying out the inventions. This description is not to be taken in a limiting sense, but is made merely for the purpose of illustrating the general principles of the inventions.

Referring to FIGS. 1 and 2, a stimulation system 10 in accordance with one embodiment of a present invention includes an electrode lead 100 and an implantable stimulator such as the implantable pulse generator ("IPG") 200. A clinician's programming unit 300, a patient remote 400 and an IPG charger (not shown) may also be provided in some instances. The exemplary electrode lead 100 includes a nerve cuff 102 (or a nerve paddle or a nerve strip or other nerve contact element) and a lead body 104 that couples the nerve cuff 102 to the IPG 200 by way of lead connector 106, with a plurality contacts 108, on the proximal end of the lead body 104 and a corresponding connector receptacle 202 on the IPG 200. The exemplary IPG 200 is discussed in greater detail below with reference to FIG. 53. The nerve cuff 102 is configured in such a manner that it may be circumferentially disposed around either the HGN trunk or a HGN branch (e.g., the HGN GM branch) as is discussed below with reference to FIGS. 3 and 4. The lead body 104 may include one or more S-shaped sections in order to provide strain relief (as shown) or may be straight. The S-shaped sections accommodate body movement at the location within the neck where the lead body 104 is implanted, thereby reducing the likelihood that the HGN will be damaged due to unavoidable pulling of the electrode lead 100 that may result from neck movements. The accommodation provided by the S-shaped sections also reduces the likelihood of fatigue damage. Additionally, although the exemplary system 10 includes a single electrode lead 100, other embodiments may include a pair of electrode leads 100 for bilateral HGN stimulation and an IPG (not shown) with two connector receptacles.

Turning to FIG. 3, and as alluded to above, the nerve cuff 102 may be positioned around the trunk 14 of the HGN 12 and used to stimulate the muscles that anteriorly move the tongue 16 and, in particular, the fascicles of the HGN 12 that innervate the tongue protrusor muscles, such as the genioglossus 18 and/or the geniohyoid muscles 20. The nerve cuff 102 is positioned on the HGN trunk 14 at a position 22 proximal to the HGN branches 24. Although there are advantages to implanting the nerve cuff 102 at this proximal position 22, i.e., reduced surgical time and effort as well as reduced risk and trauma to the patient, it introduces the problem of inadvertently stimulating other fascicles of the HGN trunk 14 that innervate muscles in opposition to the genioglossus 18 and/or the geniohyoid muscles 20, i.e., the tongue retractor muscles, e.g., the hyoglossus 26 and styloglossus muscles 28, as well as the intrinsic muscles of the tongue 16. Accordingly, while some clinicians may desire to stimulate the HGN 12 at the HGN trunk 14, others may desire to stimulate the HGN at the GM branch 24. As illustrated in FIG. 4, the same nerve cuff 102 is configured in such a manner that it may be positioned the HGN GM branch 24 instead of the trunk 14.

Figure 9:
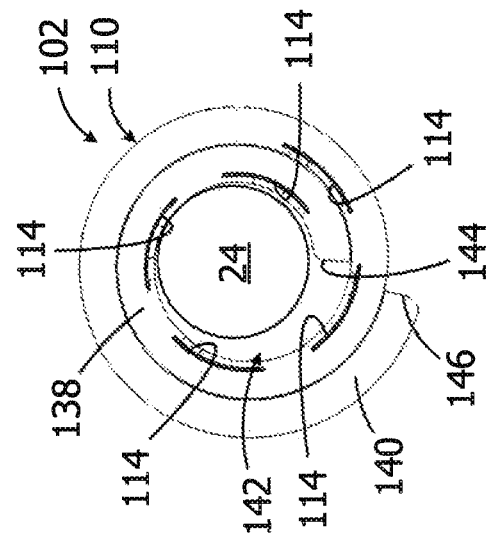
FIG. 9 is a section view of the nerve cuff illustrated in FIG. 1 in a pre-shaped furled state around a HGN branch.
Figure 11:
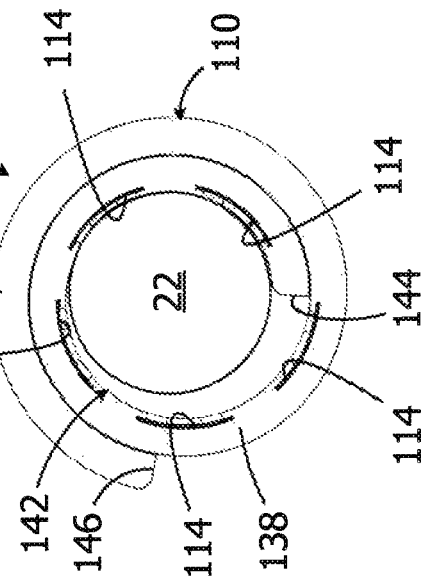
FIG. 11 is a section view of the nerve cuff illustrated in FIG. 1 in an expanded and less tightly furled state around a HGN trunk.
Figure 10:
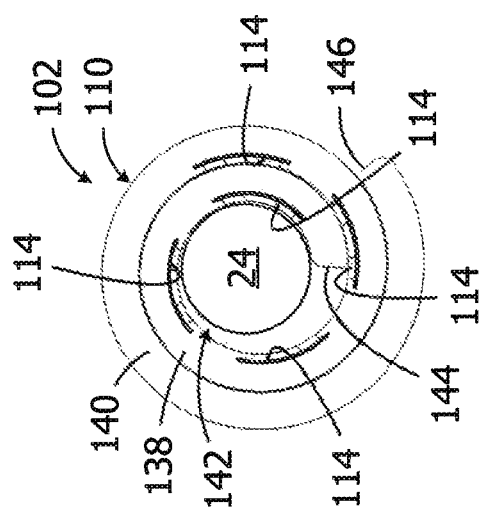
FIG. 10 is a section view of the nerve cuff illustrated in FIG. 1 in an expanded and less tightly furled state around a HGN branch.
Figure 22:
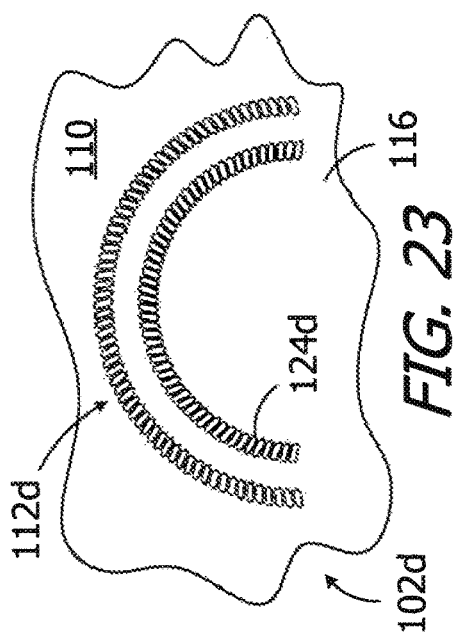
FIG. 22 is a perspective view of a portion of a nerve cuff in accordance with one embodiment of a present invention.
Figure 23:
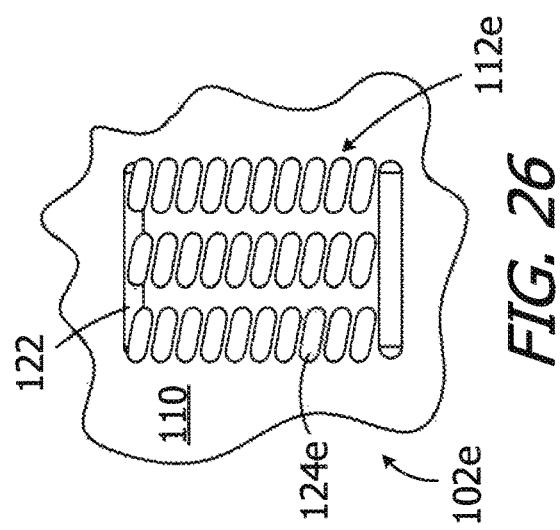
FIG. 23 is a front view of a portion of the nerve cuff illustrated in FIG. 22.
Figure 25:
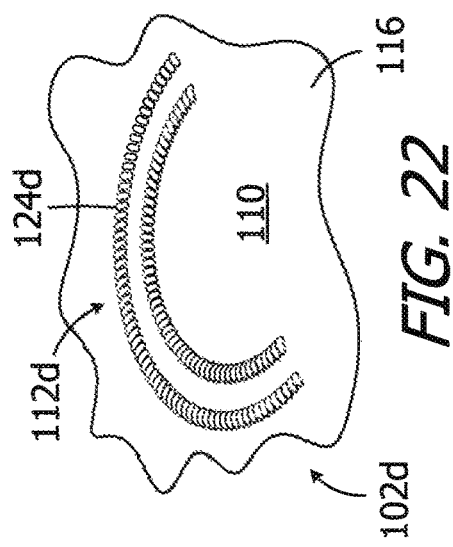
FIG. 25 is a perspective view of a portion of a nerve cuff in accordance with one embodiment of a present invention.
Figure 26:
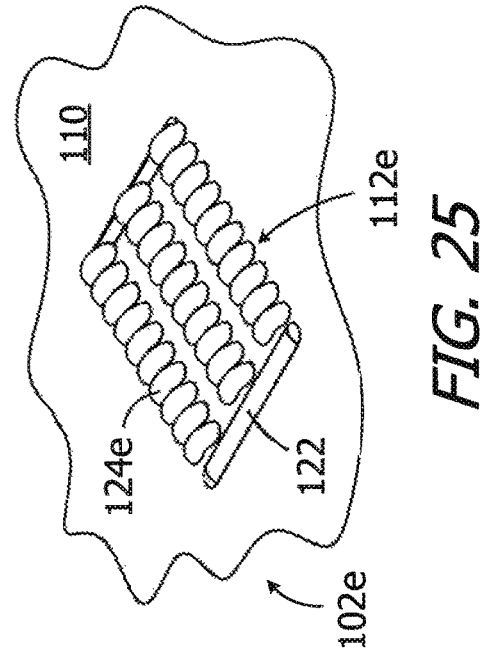
FIG. 26 is a front view of a portion of the nerve cuff illustrated in FIG. 25.
Figure 21:
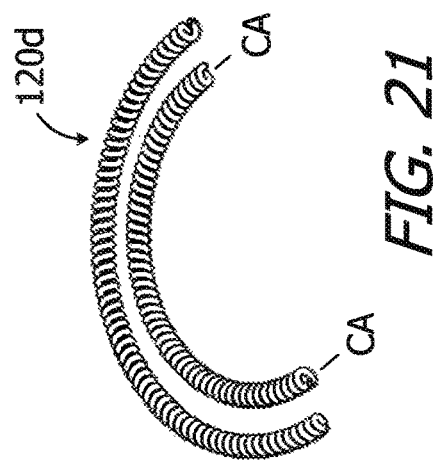
FIG. 21 is a perspective view of conductive coils in accordance with one embodiment of a present invention.

The exemplary nerve cuff 102 is shown in a flattened, unfurled state in FIGS. 5-8 and is shown in various furled states illustrated in FIGS. 9-11 that the nerve cuff will be in when it wraps around an HGN trunk 14 or HGN GM branch 24. In the illustrated implementation, the nerve cuff 102 is pre-set (or "pre-shaped") to the furled (or "curled") state illustrated in FIG. 9, and an external force may be used to partially or completely unfurl the nerve cuff 102. The nerve cuff 102 will return to the pre-shaped furled state when the force is removed and, as discussed below, may assume one of the furled states illustrated in FIGS. 9-11 depending on the size of the HGN trunk or HGN branch that the nerve cuff 102 is placed around. Various examples of nerve cuffs that are capable of assuming different sizes are disclosed in aforementioned U.S. Pat. Pub. No. 2019/0060646A1.

Referring first to FIGS. 5-8, the nerve cuff 102 includes a cuff body 110 that defines a length L and a width W that is greater than the length, first and second relatively wide electrically conductive coil contacts (or "relatively wide coil contacts" or "coil contacts") 112 on the cuff body 110 that extend in the width direction and are spaced from one another in the length direction and a plurality of relatively narrow electrically conductive flat contacts (or "relatively narrow contacts" or "contacts") 114. Such coil contacts and flat contacts may also be referred to as "electrodes." Although the number may increase or decrease in the context of other nerve applications, at least five relatively narrow contacts 114 may be spaced from one another in the width direction are located between the first and second relatively wide coil contacts 112, and there are five relatively narrow contacts 114 in the illustrated embodiment. As used herein, "relatively wide" structures are structures that are longer in the width direction than structures that are referred to as "relatively narrow" and "relatively narrow" structures are structures that are shorter in the width direction than structures that are referred to as "relatively wide." In the implementation illustrated in FIGS. 5-8, the relatively narrow contacts 114 are centered relative to the relatively wide coil contacts 112 and are aligned with one another in the length direction. In other implementations, the relatively narrow contacts may be non-centered relative to the relatively wide coil contacts 112 and/or offset from one another in the length direction. With respect to shape, and although the present inventions are not so limited, the relatively wide coil contacts 112 have an overall rectangular shape, while the relatively narrow contacts 114 are squares. Many other exemplary nerve cuffs, nerve paddles, nerve strips and other nerve contact elements with various combinations and configurations of coil contacts and/or contacts are described below with reference to FIGS. 12-45.

The exemplary cuff body 110 includes a front layer 116 that will face the HGN trunk or branch and a rear layer 118 that will face away from the HGN trunk or branch. The outer surface of the front layer 116, i.e. the top surface in FIG. 6, defines the front surface of the cuff body. The outer surface of the rear layer 118, i.e. the bottom surface in FIG. 6, defines the rear surface of the cuff body. The exemplary coil contacts 112 each include a plurality of electrically conductive coils (or "coils") 120 that are electrically connected to one another in parallel by welds 122 or any other suitable structure as is described in greater detail below with reference to FIGS. 46 and 47. The welds 122 may be located at the longitudinal ends of the coils 120, as shown, or in another location. Other exemplary coil contacts may include a single coil, two coils, or more than three coils. The coils 120 may be helical (as shown) or otherwise spiral and define a central axis CA. Although other shapes may be employed, as is discussed below, the central axes CA of the coils 120 are straight lines and the coil contacts 112 are linear. The coils 120 may be oriented in such a manner that the central axes CA are parallel to one another (as shown) or non-parallel. The central axes CA are straight in the implementation illustrated in FIGS. 5-8, but may be curved or have both straight and curved portions in other implementations. The coils 120 may be positioned on the cuff body 110 in such a manner that the central axes CA lie in a common plane such as, for example, the plane defined by the outer surface of the front layer 116 (as shown) or may lie in different planes that are defined by the length L and width W. The coils 120 project outwardly from the cuff body 110 by a distance E1 (FIG. 6) and, accordingly, have exposed portions 124 that are not covered by cuff body material or other electrically insulating material. Put another way, the coils 120 are only partially embedded in the cuff body 110, such there are embedded portions and non-embedded portions, and the exposed, non-embedded portions of the coils together define the coil contacts 112. The surface area of the exposed portions 124 may be varied in order to vary the levels of tissue interaction with the coil contacts 112, as is discussed below with reference to FIGS. 51, 52A and 52B. It should also be noted that the coil contacts provide superior bending properties, and create larger surface areas, than conventional flat contacts.

With respect to the contacts 114, the exemplary nerve cuff 102 includes five relatively narrow conductive members 126 that are located between the front layer 116 and rear layer 118. Portions of the relatively narrow conductive members 126 are exposed by way of respective relatively narrow openings 128 in the cuff body front layer 116, thereby defining the contacts 114. The openings 128 extend from the outer surface of the front layer 116 to the associated conductive members 126. The conductive members 126 may also include apertures 130 that, in conjunction with the material that forms the cuff body and enters the apertures, anchor the conductive members in their intended locations.

Referring more specifically to FIG. 8, the coil contacts 112 and contacts 114 in the exemplary nerve cuff 102 may be individually electrically connected to the plurality contacts 108 on the lead connector 106 (FIG. 2) by wires 132 that extend through the lead body 104. Each wire 132 includes a conductor 134 and an insulator 136. The conductors 134 may be connected to the rear side of the welds 122 (or coils 120) and the conductive members 126 by welding or other suitable processes. In other implementations, the coil contacts 112 may also be electrically connected to one another by a short wire. Here, only one of the coil contacts 112 will be connected to a contact 108 on the lead connector 106 by way of a wire 132. In other implementations, one of the coils 120 in one or both of the coil contacts 112 (or other coil contacts described below) may extend to the end of the lead body 104 adjacent to the associated nerve cuff and be connected to a conductor in that location, as is described below with reference to FIGS. 33-35. It should also be noted that, in the exemplary nerve cuff 102 (as well as the nerve cuffs described below), the contacts 114 are not electrically connected in series to one another and are each connected to a respective one of the wires 132. In other implementations, cables may be employed in place of the wires 132.

The cuff body 110 in the exemplary implementation illustrated in FIGS. 5-8 includes a stimulation region 138 and a compression region 140. The coil contacts 112 and flat contacts 114 are located within the stimulation region 138. There are no contacts located within the compression region 140. The compression region 140 wraps around at least a portion of the stimulation region 138 when the nerve cuff 102 is in the pre-shaped furled state and the slightly larger, expanded and less tightly furled states described below with reference to FIGS. 9-11, thereby resisting (but not preventing) expansion of the stimulation region and improving the electrical connection between the coil contacts 112 and contacts 114 and the HGN.

The exemplary cuff body 110 may be formed from any suitable material. Such materials may be biologically compatible, electrically insulative, elastic and capable of functioning in the manner described herein. By way of example, but not limitation, suitable cuff body materials include silicone, polyurethane and styrene-isobutylene-styrene (SIBS) elastomers. The cuff materials should be pliable enough to allow a clinician to unfurl the cuff body 110 (and nerve cuff 102) and place the nerve cuff around the HGN trunk (or HGN GM branch). The exemplary materials should also be resilient enough to cause the nerve cuff return to the pre-shaped furled state illustrated in FIG. 9 when the force is removed, yet flexible enough to allow the cuff body 110 (and nerve cuff 102) to instead assume the slightly larger, expanded and less tightly furled states illustrated in FIGS. 10 and 11. To that end, the furled cuff body 110 defines an inner lumen 142, in which the nerve will be located after the nerve cuff 102 wraps around the nerve, as well as lateral ends 144 and 146, which may be tapered in some implementations to reduce tissue irritation, that are respectively associated with the stimulation region 138 and the compression region 140. Comparing the state illustrated in FIG. 10 to that state illustrated in FIG. 9, the inner lumen 142 is slightly larger and the lateral end 146 is offset around the perimeter of the nerve cuff 102. Similarly, comparing the state illustrated in FIG. 11 to that state illustrated in FIG. 10, the inner lumen 142 is slightly larger and the lateral end 146 is offset around the perimeter of the nerve cuff 102. For example, the inner lumen 142 in FIG. 9 is sized to accommodate an HGN structure that has a diameter of about 2.5 mm (e.g., the HGN GM branch 24), the inner lumen 142 in FIG. 10 is sized to accommodate an HGN structure that has a diameter of about 3.0 mm (e.g., the HGN GM branch 24 in a swollen state), and the inner lumen 142 in FIG. 11 is sized to accommodate an HGN structure that has a diameter of about 4.0 mm (e.g., the HGN trunk 22). The ability to assume slightly larger, expanded and less tightly furled states, in addition to the smaller fully furled state, allows the same nerve cuff 102 to accommodate either of the larger HGN trunk 14 or a smaller HGN branch 24. The ability to assume slightly larger, expanded furled states also allows the nerve cuff to accommodate nerve swelling that may occur post-surgery and to self-adjust to a smaller state when the swelling subsides.

The exemplary cons 120 (and other cons described below) are micro-coils, i.e., coils that have an outer diameter of less than about 0.050 inch. In the exemplary context of a nerve cuff, the cons may be formed from a solid wire or multi-filar cable that is from about 0.001 inch to about 0.015 inch in diameter and is about 0.006 inch in the illustrated embodiments. The coils may also be multi-filar coils, i.e., cons that are formed from multiple wires or cables. As used herein in the context of dimensions, the word "about" means±10-20%. The outer diameter of the coils 120 may range from about 0.005 inch to about 0.050 inch and is about 0.020 inch in the illustrated embodiments. The coil pitch may range from tightly wound (i.e., no gaps) to about 0.050 inch and is about 0.008 inch in the illustrated embodiments. The exemplary coils 120 are also about 0.50 inch long (in the width W direction). Suitable materials for the coils 120 (and other coils described below) and conductive members 126 include, but are not limited to, biocompatible and biostable metals such as platinum-iridium, palladium and its alloys and tantalum and its alloys. Less noble materials, such as titanium and its alloys or 316LVM stainless steel, with a barrier coating such as platinum or titanium nitride, may also be employed. The coils 120 (and other coils described below) and conductive members 126 may also be treated with a surface area enhancing coating such as, for example, platinum black, platinum gray, titanium nitride, or iridium oxide, etc.

It should also be noted here that the coil contacts 112 are sized such that they extend completely around the inner lumen 142, i.e., 360° or more around the longitudinal axis of the inner lumen, when the cuff body 110 is in the fully furled state illustrated in FIG. 9 that accommodates an HGN structure having a diameter of about 2.5 mm. Viewed as a group, the relatively narrow contacts 114 also extend completely around the inner lumen 142 when the when the cuff body 110 is in the fully furled state illustrated in FIG. 9. The coil contacts 112 also extend substantially around the inner lumen 142, i.e., at least 288° in some examples and 360° or more in other examples, around the longitudinal axis of the inner lumen, when the cuff body 110 is in the expanded and less tightly furled state illustrated in FIG. 11 that accommodates an HGN structure having a diameter of about 4.0 mm. Viewed as a group, the relatively narrow contacts 114 also extend substantially around the inner lumen 142 when the when the cuff body 110 is in the expanded and less tightly furled state illustrated in FIG. 11.

The dimensions of the present nerve cuffs, including the various elements thereof, may by any dimensions that result in the nerve cuffs functioning as intended. With respect to the dimensions of the cuff body 110 of the exemplary nerve cuff 102, and referring to FIG. 5, the cuff body is about 1.1 inches wide and about 0.34 inch long. The width of the stimulation region 138 is about 0.6 inch, while the width of the compression region 140 is about 0.5 inch. The coil contacts 112 are same size, and the relatively narrow contacts 114 are the same size, in the illustrated implementation. In other implementations, the coil contacts 112 may be different sizes and/or the relatively narrow contacts 114 may be different sizes. In the embodiment illustrated in FIG. 5, the width W1 of the coil contacts 112 is about 0.5 inch, the length L1 is about 0.04 inch, the distance D1 between the coil contacts 112 is about 0.2 inches. The relatively narrow contacts 114 width W2 is about 0.07 inch and length L2 is about 0.07 inch, the is about 0.06 inches and the distance D2 between the relatively narrow contacts 114 is about 0.05 inch. The distance D2 may also be increased or decreased as desired to accomplish various stimulation objectives. The distance D3 between the relatively narrow contacts 114 and the relatively wide contacts 112 is about 0.07 inch.

Another exemplary nerve cuff is generally represented by reference numeral 102*a* in FIGS. 12-14. Nerve cuff 102*a* is substantially similar to nerve cuff 102 and similar elements are represented by similar reference numerals. For example, the nerve cuff 102*a* may form part of an electrode lead that may be connected to the IPG 200, or other suitable device, and employed in stimulation methodologies such as those described above. The nerve cuff 102*a* includes a cuff body 110*a* with a front layer 116, a rear layer 118, two coil contacts 112, and a plurality of relatively narrow contacts 114 that are defined by portions of the conductive members 126 that are exposed by way of narrow openings 128 in the cuff body front layer 116. The cuff body 110 also has a stimulation region 138 and a compression region 140. The coil contacts 112 and contacts 114 may be individually electrically connected to the plurality contacts 108 on the lead connector 106 (FIG. 2) by wires that extend through the lead body 104 in the manner described above with reference to FIG. 8 or other manners described below.

Here, however, coil contacts 112 are entirely located between the exposed surfaces of the front layer 116 and rear layer 118 and portions of the coil contacts are exposed by way of openings 148 that extend through the outer surface of the front layer 116 and into the cuff body 110*a* by a distance E2. Straps 150, which are located between the openings 148 and extend across the coils 120 in the length direction, reduce the likelihood of delamination. The openings 148 define exposed portions 124 of the coils 120 that are not embedded in the cuff body 110*a* and covered by cuff body material (or other electrically insulating material). Put another way, the exposed non-embedded portions of the coils 120 are located within the openings 148. The surface area of the exposed portions 124 may be varied in order to vary the levels of tissue interaction with the coil contacts 112, as is discussed below with reference to FIGS. 51, 52A and 52B. In still other implementations, the straps 150 may be omitted and the openings 148 may be combined into one large opening that exposes all of the coil contact 112 (or almost all of the coil contact 112).

Although the exemplary neve cuffs 102 and 102*a* include relatively wide coil contacts 112 with three linear coils, and five flat relatively narrow contacts, the present inventions are not so limited. Nerve cuffs, nerve paddles, nerve strips and other nerve contact elements in accordance with the present inventions may include electrically conductive coil contacts of any suitable shape, size, location and combination. By way of example, but not limitation, one or more of the helical coil contacts illustrated in FIGS. 15-35 may be employed in a nerve cuff, a nerve paddle, a nerve strip or other nerve contact element.

Referring first to FIGS. 15-17, the planar spiral (or "spiral") helical coil 120*b* in the exemplary nerve cuff 102*b* has a spiral central axis CA and projects outwardly from the outer surface of the front layer 116 of the cuff body 110. The exposed portions 124*b* of the spiral helical coil 120*b* that are not covered by cuff body material (or other electrically insulating material) together define a spiral coil contact 112*b*.

Turning to FIGS. 18-20, the m-shaped helical coil 120*c* of the exemplary nerve cuff 102*c* has an m-shaped central axis CA and projects outwardly from the outer surface of the front layer 116 of the cuff body 110. The exposed portions 124*c* of the m-shaped helical coil 120*c* that are not covered by cuff body material (or other electrically insulating material) together define an m-shaped coil contact 112*c*.

Semi-circular (or otherwise arcuate) helical coil contacts may also be employed. The semi-circular helical coils 120*d* illustrated in FIG. 21 may be included in the exemplary nerve cuff 102*d* (FIGS. 22 and 23) in such a manner that exposed portions 124*d* of the coils 120*d* project outwardly from the outer surface of the front layer 116 of the cuff body 110. The exposed portions 124*d* are not covered by cuff body material (or other electrically insulating material) and together define semi-circular coil contacts 112*d*.

Figure 24:
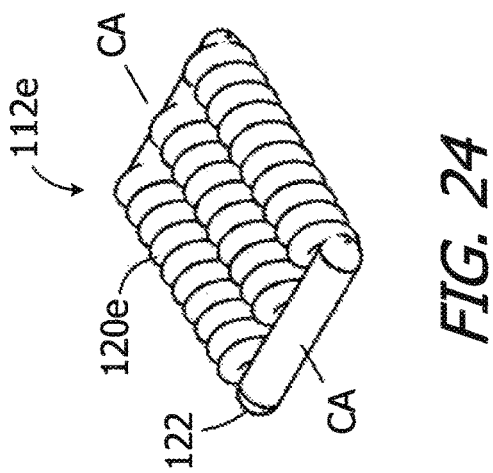
FIG. 24 is a perspective view of conductive coils in accordance with one embodiment of a present invention.

The assembly defined by coils 120*e* and welds 122 illustrated in FIG. 24 is essentially identical to the above-described assembly defined by coils 120 and welds 122 (FIGS. 5-8), but for the use of coils 120*e* that are substantially shorter in the direction of the central axis CA than the coils 120. The coils 120*e* may be incorporated into the exemplary nerve cuff 102*e* illustrated in FIGS. 25 and 26 in such a manner that there are exposed portions 124*e* that are not covered by cuff body material (or other electrically insulating material). The exposed portions 124*e* project outwardly from the outer surface of the front layer 116 of the cuff body 110 and together define coil contacts 112*e*.

Coil contacts having wave-like shapes, such as sinusoidal-shaped coil contacts, may also form part of a nerve cuffs, nerve paddles, nerve strips, and other nerve contact elements. Referring to FIGS. 27-29, the sinusoidal-shaped coil 120*f* in the exemplary nerve cuff 102*f* has a sinusoidal central axis CA and projects outwardly from the outer surface of the front layer 116 of the cuff body 110, which results in exposed portions 124*f* that are not covered by cuff body material (or other electrically insulating material). The exposed portions 124*f* together define a sinusoidal coil contact 112*f*.

Circular coil contacts (and other coil contacts that have closed geometric shapes such as, for example, ovals, ellipses, and rectangles) may be employed in some instances. For example, the circular helical coils 120*g* illustrated in FIG. 30 may be included in the exemplary nerve cuff 102*g* illustrated in FIGS. 31 and 32. The circular coils 120*g*, which have circular central axes (not shown), project outwardly from the outer surface of the front layer 116 of the cuff body 110 and have exposed portions 124*g*. The exposed portion 124*g* are not covered by cuff body material (or other electrically insulating material) and together define circular coil contacts 112*g*.

It should also be noted that helical coils may be used in place of some or all of the wires 132 (FIG. 8) that extend from the present coil contacts. Here, the helical coils include two integral coil parts that are on different portions of the associated central axis. The first part of the coil is the part that includes the exposed portions which define the coil contact, while the second part is entirely embedded within the cuff body between the front and rear outer surfaces and is not exposed. The second part may extend through the lead body 104 (FIG. 1) to the lead connector 106 (FIG. 2) or simply to a region of the cuff body 110 where it can be connected to the wires 132.

To that end, and referring for example to FIGS. 33 and 34, the exemplary nerve cuff 102*h* includes a coil with first and second parts 120*h*-1 and 120*h*-2. Both parts are entirely located between the exposed surfaces of the front layer 116 and rear layer 118 (FIG. 6). The exemplary coil part 120*h*-1 is m-shaped and is partially exposed by way of an opening 148*h* that extends into the cuff body 110*h* and through front layer 116. The exposed portions 124*h*-1 of the coil part 120*h*-1 that are not covered by cuff body material (or other electrically insulating material) define an m-shaped coil contact 112*h*. The second coil part 120*h*-2 extends from the opening 148, through a portion of the cuff body 110*h*, and either through the lead body 104 (FIG. 1) to the lead connector 106 (FIG. 2) or simply to a region of the cuff body 110*h* where it can be connected to a wire 132.

Turning to FIG. 35, the exemplary assembly illustrated therein includes two of the above-described coils 120 and a third coil 120*i* with first and second parts 120*i*-1 and 120*i*-2. All three of the coils are connected to one another by a weld 122, while only coils 120 are connected by weld 122*i*. Coil 120*i* is not connected to weld 122*i*. The first coil part 120*i*-1 extends from the weld 122 to a point aligned with the weld 122*i*, while the second coil part 120*i*-2 extends from the end of the first coil part and may be used to connect the coils 120 and 120*i* to either the lead connector 106 (FIG. 2) or a wire 132, as described above, when incorporated into a nerve cuff.

As alluded to above, the present coil contacts and flat contacts may combined and/or modified in any manner that is suitable for the intended application. The contacts on the associated nerve cuffs, nerve paddles, nerve strips, and other nerve contact elements may all be the same, may be mixed and matched as desired, may be of different sizes, and the number of contacts on a particular may vary as desired. By way of example, but not limitation, various coil contact combinations are illustrated in FIGS. 36-45 in the exemplary context of nerve cuffs and nerve paddles. The wiring and other features that are not mentioned in the context of FIGS. 36-45 in the interest of brevity may be the same as that described in the context of nerve cuff 102 (FIGS. 1-8) and/or cuff 102*h* (FIGS. 33 and 34) and/or the assembly illustrated in FIG. 35. Additionally, the coil contacts may project outwardly from the cuff body (as shown in FIGS. 36-45) or may be exposed by way of one or more openings in a manner similar to that described above with reference to FIGS. 12-14. It should also be noted that the coil contacts and flat contacts may either be electrically independent from one another (as shown in FIG. 8), or some or all of the contacts may be electrically common.

Referring first to FIG. 36, the stimulation region 138 of the exemplary nerve cuff 102*j* includes four of the sinusoidal coil contacts 112*f*. The contacts 112*f* may extend in the length L direction and be equally spaced in the width W direction, as shown, or may be reoriented and moved as desired. The sinusoidal coil contacts 112*f* are defined by exposed portions 124*f* of the sinusoidal coils 120*f* (FIG. 27) that project outwardly from the outer surface of the front layer 116 of the cuff body 110, as is described above.

As illustrated for example in FIG. 37, the stimulation region 138 of the exemplary nerve cuff 102*k* includes six spiral helical coil contacts 112*b* that are arranged in two rows of three. The rows are offset in the width W direction. The coil contacts 112*b* in each row may be aligned with one another in the length L direction and equally spaced in the width W direction, as shown, or may be reoriented and moved as desired. The spiral coil contacts 112*b* are defined by exposed portions 124*b* of spiral helical coils 120*b* (FIG. 15) that project outwardly from the outer surface of the front layer 116 of the cuff body 110, as is described above.

The stimulation region 138 of the exemplary nerve cuff 102*l* illustrated in FIG. 38 includes three m-shaped helical coil contacts 112*c*. The m-shaped contacts 112*c* may be oriented such that the straight portions parallel to the width W direction, and positioned such that they are aligned in the length L direction and are equally spaced in the width W direction (as shown). They may also be reoriented and moved as desired. The m-shaped coil contacts 112*c* are defined by exposed portions 124*c* of the spiral helical coils 120*c* (FIG. 18) that project outwardly from the outer surface of the front layer 116 of the cuff body 110, as is described above.

Turning to FIG. 39, the stimulation region 138 of the exemplary nerve cuff 102*m* includes two sinusoidal helical coil contacts 112*f'*. The sinusoidal contacts 112*f'*, which are identical to sinusoidal contacts 112*f* but for additional undulations, may extend in the width W direction and are spaced in the length L direction. Four pairs of circular helical coil contacts 112*g*, which have contacts arranged one inside the other in each pair, are located between the sinusoidal contacts 112*f'*. The pairs of circular contacts 112*g* may be positioned such that they are aligned in the length L direction, equally spaced in the width W direction and centered relative to the sinusoidal contacts 112*f'* (as shown) and may be reoriented and moved as desired. As such, the exemplary nerve cuff 102*m* includes first and second relatively wide helical coil contacts 112*f'* and a plurality of relatively narrow helical coil contacts 112*g* therebetween. The helical coil contacts 112*f'* and 112*g* are defined by exposed portions 124*f* and 124*g* of the helical coils 120*f* and 120*g* (FIGS. 27 and 30) that project outwardly from the outer surface of the front layer 116 of the cuff body 110, as is described above.

Figure 40:
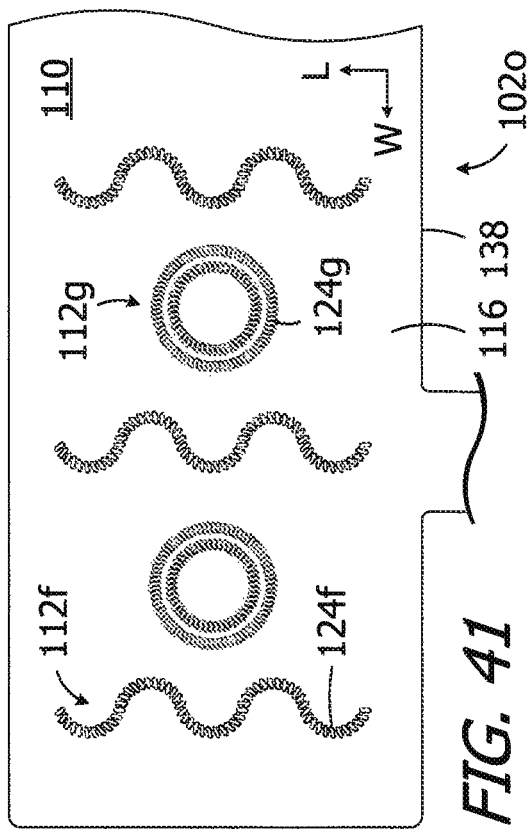
FIG. 40 is a front view of a nerve cuff in accordance with one embodiment of a present invention.
Figure 41:
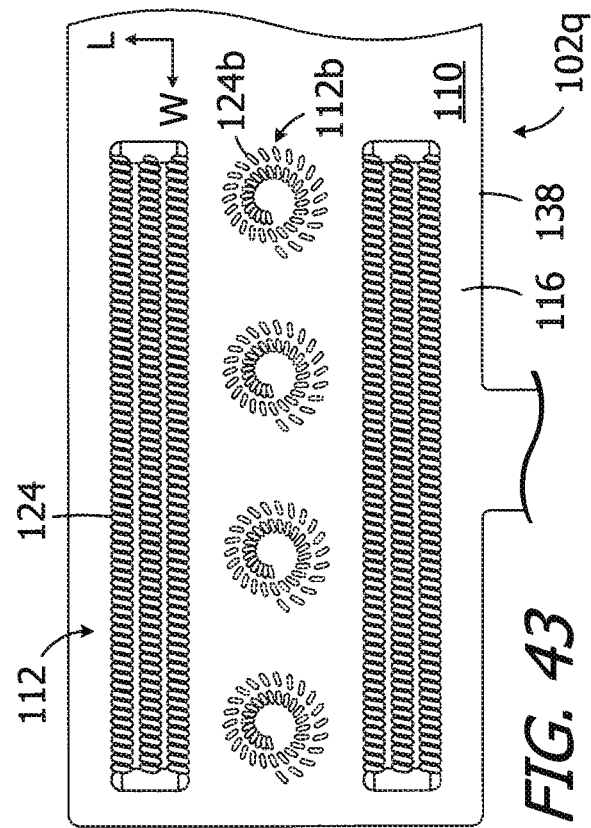
FIG. 41 is a front view of a nerve cuff in accordance with one embodiment of a present invention.

Referring to FIG. 40, the exemplary nerve cuff 102*n* has a stimulation region 138 with two pairs of semi-circular helical coil contacts 112*d* that are aligned in the length L direction and spaced in the width W direction. Three sinusoidal helical coil contacts 120*f* are located between the two pairs of semi-circular contacts 112*d*. The sinusoidal contacts 120*f* extend in the width W direction and may be equally spaced in the length L direction, as shown, or may be reoriented and moved as desired. As such, the exemplary nerve cuff 102*n* includes first and second relatively long helical coil contacts 112*d* and a plurality of relatively short helical coil contacts 112*f* therebetween. The helical coil contacts 112*d* and 112*f* are defined by exposed portions 124*d* and 124*f* of the helical coils 120*d* and 120*f* (FIGS. 21 and 27) that project outwardly from the outer surface of the front layer 116 of the cuff body 110, as is described above. The stimulation region 138 of the exemplary nerve cuff 102*o* illustrated in FIG. 41 includes three sinusoidal helical coil contacts 112*f*. The contacts 112*f* may extend in the length L direction and equally spaced in the width W direction, as shown, or may be reoriented and moved as desired. Pairs of circular helical coil contacts 112*g*, arranged one inside the other in each pair, are located between the sinusoidal contacts 112*f* and may be positioned such that they are aligned in the length L direction and are equally spaced between the sinusoidal contacts 112*f* in the width W direction. As such, the exemplary nerve cuff 102*o* includes first and second relatively long helical coil contacts 112*d* and a plurality of relatively short helical coil contacts 112*f* therebetween. The helical coil contacts 112*f* and 112*g* are defined by exposed portions 124*f* and 124*g* of the helical coils 120*f* and 120*g*

(FIGS. 27 and 30) that project outwardly from the outer surface of the front layer 116 of the cuff body 110, as is described above.

Figure 42:
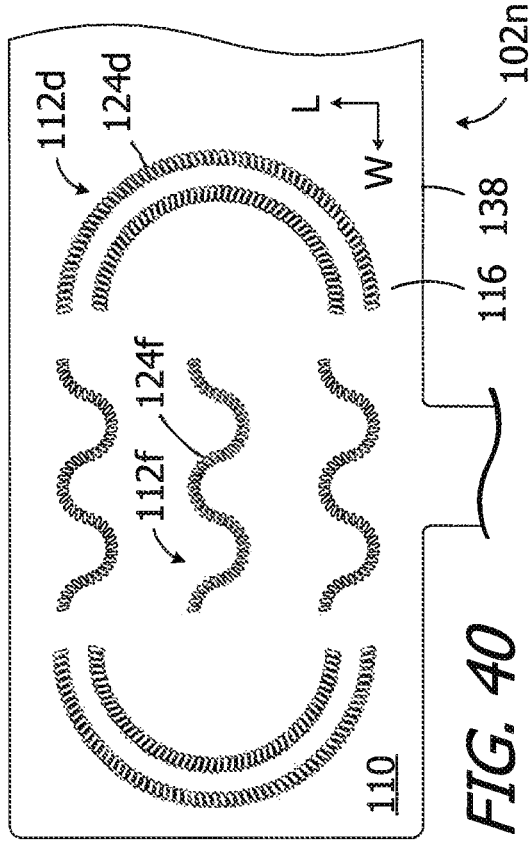
FIG. 42 is a front view of a nerve cuff in accordance with one embodiment of a present invention.

As illustrated in FIG. 42, the exemplary nerve cuff 102p includes first and second relatively wide coil contacts 112 that extend in the width W direction and are spaced from one another in the length L direction and four relatively narrow m-shaped coil contacts 112c between the coil contacts 112. The m-shaped coil contacts 112c may be centered relative to the coil contacts 112, oriented such that the straight portions parallel to the width W direction, and positioned such that they are equally spaced in the width W direction, as shown, and may be reoriented and moved as desired. As such, the exemplary nerve cuff 102p includes first and second relatively wide helical coil contacts 112 and a plurality of relatively narrow helical coil contacts 112c therebetween. The helical coil contacts 112 and 112c are defined by exposed portions 124 and 124c of the helical coils 120 and 120c (FIGS. 5-8 and 18) that project outwardly from the outer surface of the front layer 116 of the cuff body 110, as is described above.

Figure 43:
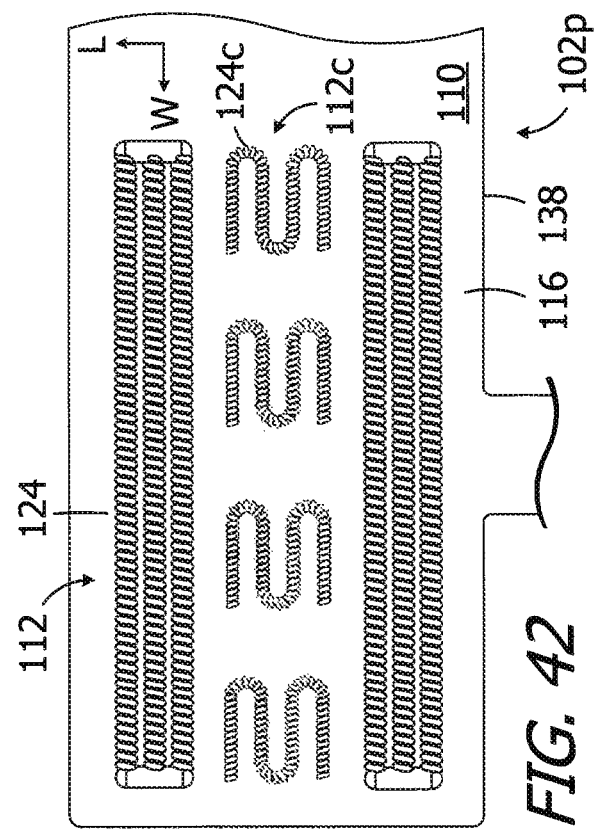
FIG. 43 is a front view of a nerve cuff in accordance with one embodiment of a present invention.

Similarly, the exemplary nerve cuff 102q illustrated in FIG. 43 includes first and second relatively wide coil contacts 112 that extend in the width W direction and are spaced from one another in the length L direction and four relatively narrow spiral helical coil contacts 112b between the coil contacts 112. The spiral coil contacts 120b may be centered relative to the coil contacts 112 and positioned such that they are equally spaced in the width W direction, as shown, and may be reoriented and moved as desired. As such, the exemplary nerve cuff 102q includes first and second relatively wide helical coil contacts 112 and a plurality of relatively narrow helical coil contacts 112b therebetween. The helical coil contacts 112 and 112b are defined by exposed portions 124 and 124b of the helical coils 120 and 120b (FIGS. 5-8 and 15) that project outwardly from the outer surface of the front layer 116 of the cuff body 110, as is described above.

Figure 44:
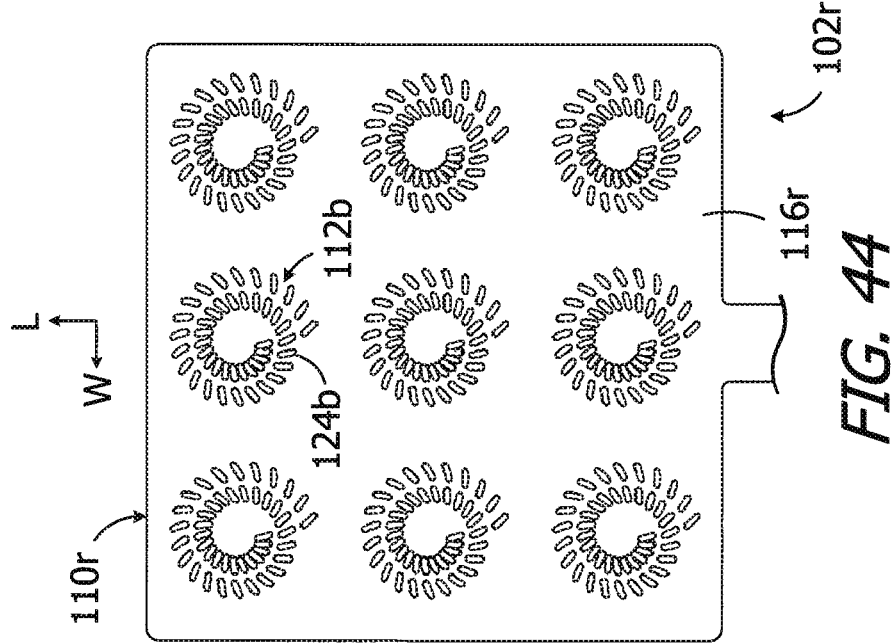
FIG. 44 is a front view of a nerve paddle in accordance with one embodiment of a present invention.

The exemplary nerve paddle 102r illustrated in FIG. 44 includes a paddle body 110r with a front layer 116r and a plurality of spiral helical coil contacts 112b. There are nine spiral contacts 112b, arranged in three rows of three coils, and the contacts are equally spaced in the length L direction and the width W direction, as shown, and may be reoriented and moved as desired. The spiral contacts 112b are defined by exposed portions 124b of the spiral helical coils 120b (FIG. 15) that project outwardly from the outer surface of the front layer 116 of the cuff body 110, as is described above.

Figure 45:
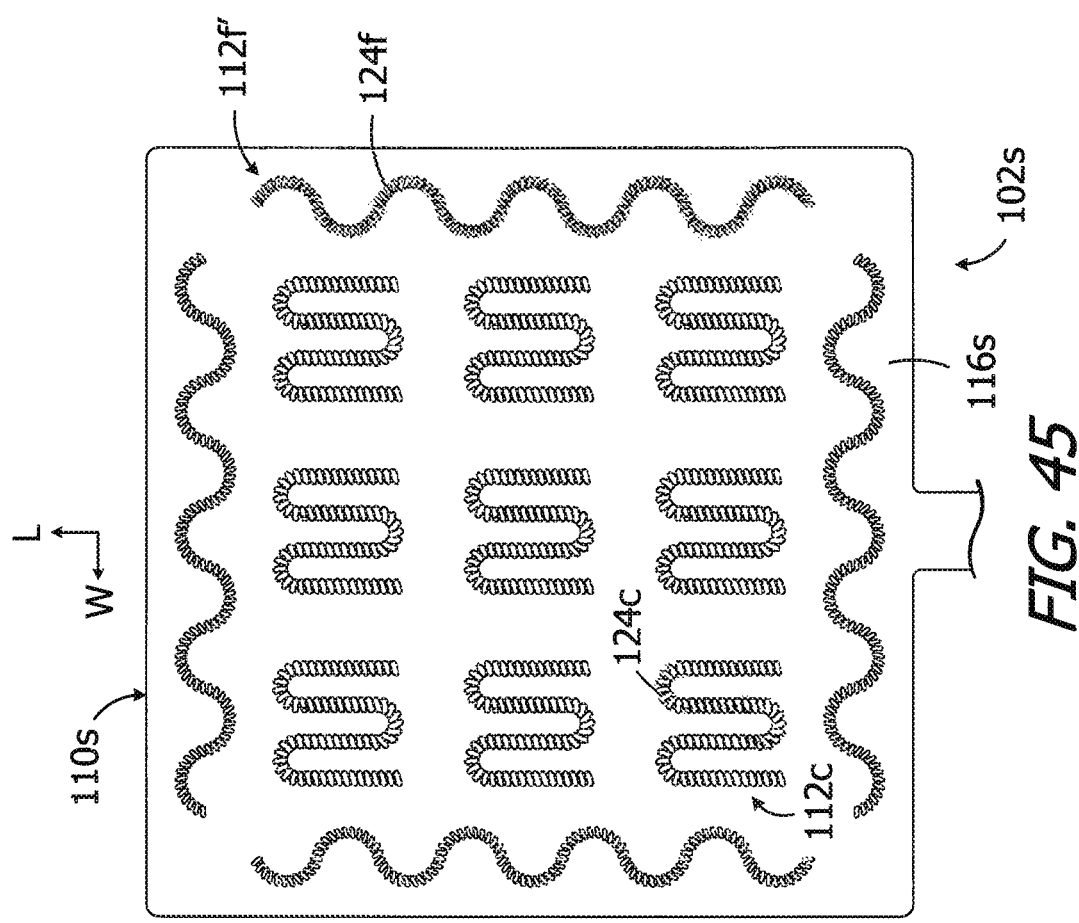
FIG. 45 is a front view of a nerve paddle in accordance with one embodiment of a present invention.

Turning to FIG. 45, the exemplary nerve paddle 102s illustrated therein includes a paddle body 110s with a front layer 116s, a plurality of sinusoidal helical coil contacts 120f, and a plurality of m-shaped helical coil contacts 112c. There are four sinusoidal coil contacts 112f, with two that extend in the width W direction and are spaced in the length L direction and two that extend in the length L direction and are spaced in the width W direction. There are nine m-shaped coil contacts 112c, located between the sinusoidal contacts 112f and arranged in three rows of three contacts, and the contacts are equally spaced in the length L direction and the width W direction. As such, the exemplary nerve paddle 102s includes respective pairs of relatively wide and relatively long helical coil contacts 112f and a plurality of relatively short and narrow helical coil contacts 112c therebetween. The helical coil contacts 112c and 112f are defined by exposed portions 124c and 124f of the helical coils 120c and 120f (FIGS. 18 and 27) that project outwardly from the outer surface of the front layer 116 of the cuff body 110, as is described above.

Turning to manufacturing, the exemplary helical coils may include structures that facilitate connections to one another and/or to wires. For example, the helical coil 120 illustrated in FIG. 46 includes a solid ball 121 formed from the same material as the remainder of the coil. The solid ball 121 may be formed by a welding technique such as the laser pulse welding. Referring also to FIG. 47, three of the solid balls 121 may be welded together to form the weld 122, thereby mechanically and electrically connecting the ends of the associated coils 120 to one another.

The exemplary nerve cuff 102 (and other nerve cuffs and nerve paddles described herein) may be manufactured through a process that employs a cuff blank such as the cuff blank 101 illustrated in FIGS. 48 and 49. The cuff blank 101 includes the various components of the nerve cuff 102, i.e., cuff body 110, the coils 120, the conductive members 126, and the wires 132 (not shown). The coils 120 and conductive members 126 are embedded within the cuff blank 101. In particular, and in addition to the cuff body 110, the cuff blank 101 includes a cap 111 that covers the portions of the coils 120 that are not below outer surface of the front layer 116. The cap 111 is formed when the coils 120 are molded into the corresponding portion of the cuff body 110. A primer may be applied to the coils 120 prior to molding to enhance the adhesion of the cuff body material to the coils 120. Portions of cuff body front layer 116 may be removed to form the openings 128 that expose the portions of the conductive members 126 that define the contacts 114. In other implementations, the front layer 116 may include preformed openings 128.

With respect to the coil contacts 112, some or all of the cap 111 may be removed to expose portions 124 of the coils 120 as shown in FIG. 50. The cross-sectional shape of the exposed portions 124 corresponds to the cross-sectional shape of the wire from which the coil 120 is formed. The cross-sectional shape may be curved with an apex that defines the distance E1, and is semi-circular in the illustrated implementation. Suitable removal techniques include, but are not limited to, direct mechanical abrasion processes (e.g., abrasive wheel and wire brush-based processes), blasting with soda, dry ice, and/or other abrasive media (e.g., alumina and silicone carbide), and laser ablation. The amount of the cap 111 that is removed determines, for a given coil, the surface area of the exposed portions 124. To that end, and referring to FIG. 51, the exemplary coil 120 may be formed from a wire that is about 0.006 inch in diameter that is wound into a 0.50 inch long helical coil with outer diameter of about 0.020 inch and a coil pitch of about 0.008 inch. The coil 120 is positioned within the blank 101 in such a manner that ½ of the coil is above the front layer outer surface 116os, and ½ of the coil is below the front layer outer surface 116os. As such, up to 0.01 inch of the coil circumference may be exposed and, for the purposes of explanation only, incremental removal depths of 0.001 inch are shown in FIG. 51.

Figure 52B:
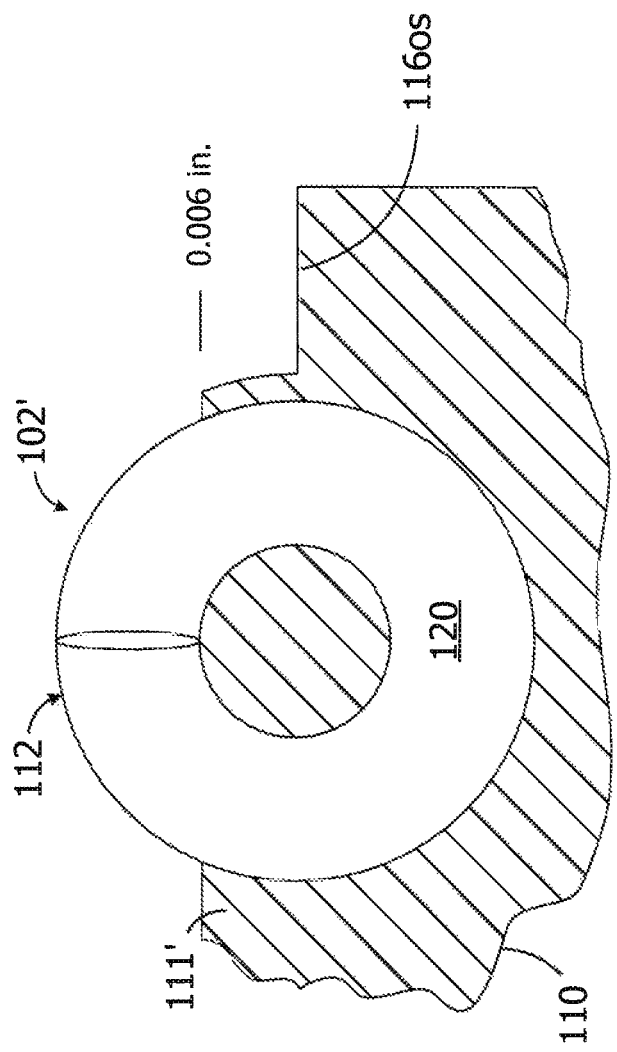
FIG. 52B is a partial section view showing a portion of a nerve cuff formed from the blank illustrated in FIG. 49.

For example, in those instances where the entire ½ of the coil circumference is exposed (which corresponds to a 0.010 inch removal depth as shown in FIG. 52A), the exposed surface area of one of the exemplary coils 120 is 0.026 inch$^2$, and total the exposed surface area of all three coils 120 in the contact 112 (FIG. 5) is 0.079 inch$^2$. Alternatively, in those instances where the removal depth is 0.006 inch (as shown in FIG. 52B), the exposed surface area of one of the exemplary coils 120 is 0.016 inch$^2$, and total the exposed surface area of all three coils 120 in the contact 112 (FIG. 5)

is 0.047 inch². By way of comparison, a flat contact occupying a similar overall footprint as the three-coil contact 112 would have a width of 0.5 inch and a length of 0.04 inch (note dimensions W1 and L1 in FIG. 5) and, accordingly, a surface area of 0.02 inch².

Figure 53:
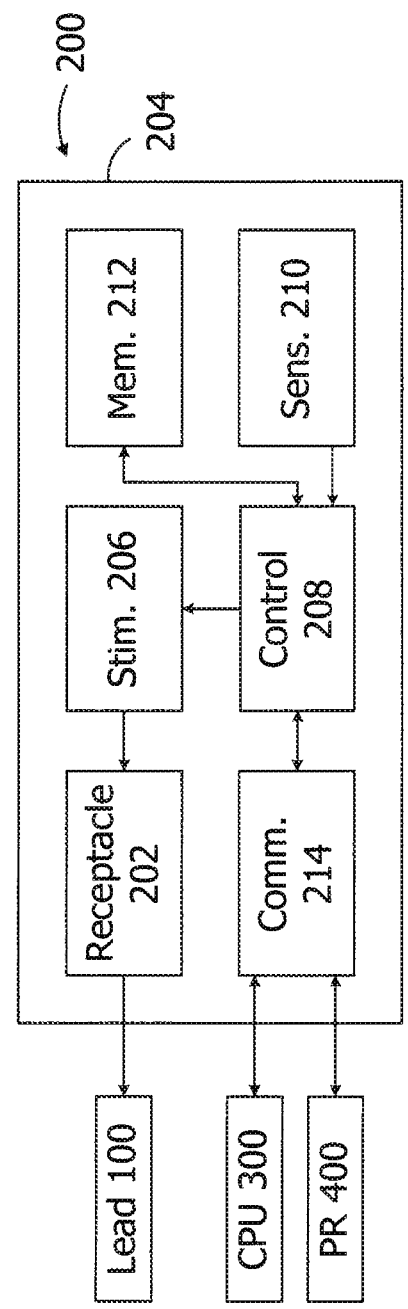
FIG. 53 is a block diagram of the stimulation system illustrated in FIG. 1.

Turning to FIG. 53, the exemplary IPG 200 includes the aforementioned receptacle 202, a hermetically sealed outer case 204, and various circuitry (e.g., stimulation circuitry 206, control circuitry 208, sensing circuitry 210, memory 212, and communication circuitry 214) that is located within the outer case 204. The outer case 204 may be formed from an electrically conductive, biocompatible material such as titanium. The stimulation circuitry 206, which is coupled to the coil contacts 112 and flat contacts 114 by way of the connector 106, receptacle 202 and wires 136, is configured to deliver stimulation energy to the HGN. The control circuitry 208 controls when and for how long the stimulation circuitry 206 applies stimulation, the intensity of the stimulation, the mode of stimulation (i.e., monopolar, bipolar or tripolar), and the particular contacts that are used in the stimulation. In the monopolar stimulation, at least a portion of the outer case 204 functions as a return electrode in the electrical circuit that also includes one or more of the coil contacts 112 and contacts 114. In bipolar stimulation, the outer case 204 is not part of the electrical circuit and current instead flows from one of the coil contacts 112 and contacts 114 to one of the other coil contacts 112 and contacts 114. In tripolar stimulation, the outer case 204 is not part of the electrical circuit and current flows from one or more of the coil contacts 112 and contacts 114 to more than one of the other coil contacts 112 and contacts 114. The contacts that the current flows to form part of the return path for the stimulation energy, as do the associated wires connected thereto. The stimulation may also be predominantly axial vector stimulation, predominantly radial vector stimulation, or a hybrid of axial vector and radial vector.

It should also be noted here that in most instances, contacts that are entirely separated from (and electrically disconnected from) the associated nerve by the cuff body will not be used by the IPG for current transmission and return. For example, when the exemplary nerve cuff 102 is in less lightly furled state illustrated in FIG. 10, one of the contacts 114 is entirely separated from the GM branch 24 by the electrically non-conductive cuff body 110 and will not be used for current transmission or return. Such contacts may be identified by, for example, measuring the impedance at each contact.

The sensing circuitry 210 in the illustrated embodiment may be connected to one or more sensors (not shown) that are contained within the outer case 204. Alternatively, or in addition, the sensors may be affixed to the exterior of the outer case 204 or positioned at a remote site within the body and coupled to the IPG 200 with a connecting lead. The sensing circuitry 210 can detect physiological artifacts that are caused by respiration (e.g., motion or ribcage movement), which are proxies for respiratory phases, such as inspiration and expiration or, if no movement occurs, to indicate when breathing stops. Suitable sensors include, but are not limited to, inertial sensors, bioimpedance sensors, pressure sensors, gyroscopes, ECG electrodes, temperature sensors, GPS sensors, and combinations thereof. The memory 212 stores data gathered by the sensing circuitry 210, programming instructions and stimulation parameters. The control circuitry 208 analyzes the sensed data to determine when stimulation should be delivered. The communication circuitry 214 is configured to wirelessly communicates with the clinician's programming unit 300 and patient remote 400 using radio frequency signals.

The control circuitry 208 may apply stimulation energy to either the HGN truck or an HGN branch (e.g. the HGN GM branch) in various stimulation methodologies by way of the cuff 102 when the patient is in the inspiratory phase of respiration, and other conditions for stimulation are met, thereby causing anterior displacement of the tongue to keep the upper airway unobstructed. The control circuitry 208 causes the stimulation circuitry 206 to apply stimulation in the form of a train of stimulation pulses during these inspiratory phases of the respiratory cycle (or slightly before the inspiration and ending at the end of inspiration) and not the remainder of the respiration cycle. The train of stimulus pulses may be set to a constant time duration or may change dynamically based on a predictive algorithm that determines the duration of the inspiratory phase of the respiratory cycle.

Although the inventions disclosed herein have been described in terms of the preferred embodiments above, numerous modifications and/or additions to the above-described preferred embodiments would be readily apparent to one skilled in the art. It is intended that the scope of the present inventions extend to all such modifications and/or additions. The inventions include any and all combinations of the elements from the various embodiments disclosed in the specification. The scope of the present inventions is limited solely by the claims set forth below.

We claim:

1. An electrode lead, comprising:
    an elongate lead body having a proximal end and a distal end; and
    a nerve cuff including
        a biologically compatible, elastic, electrically insulative cuff body affixed to the distal end of the lead body, the cuff body being configured to be circumferentially disposed around a nerve, having a pre-set furled state that defines an inner lumen, being movable to an unfurled state, including a front outer surface that faces the inner lumen when the cuff body is in the furled state and a rear outer surface, and defining a length, a length direction, a width in the unfurled state that is greater than the length, and a width direction, and
        a plurality of electrically conductive coils that extend in the width direction, that are electrically connected to one another in parallel, and that are partially embedded in the cuff body such that each coil has coiled non-embedded portions, which together define a coil contact that projects outwardly from the front outer surface toward the inner lumen when the cuff body is in the furled state, and embedded portions.

2. An electrode lead as claimed in claim 1, wherein
    the plurality of electrically conductive coils comprises a first plurality of electrically conductive coils together define a first coil contact; and
    the electrode lead further comprises a second plurality of electrically conductive coils that extend in the width direction, that are electrically connected to one another in parallel, and that are partially embedded in the cuff body such that each coil has coiled non-embedded portions, which together define a second coil contact that projects outwardly from the front outer surface toward the inner lumen when the cuff body is in the furled state, and embedded portions.

3. An electrode lead as claimed in claim 2, wherein
    each of the electrically conductive coils of the second coil contact defines a central axis; and the central axes of at least two of the plurality of electrically conductive coils of the second coil contact are parallel to one another.

4. An electrode lead as claimed in claim 2, wherein
the first and second coil contacts are relatively wide coil contacts that are separated from one another in the length direction; and
the electrode lead further comprises a plurality of relatively narrow contacts that are located between the relatively wide coil contacts.

5. An electrode lead as claimed in claim 4, wherein
the relatively narrow contacts comprise flat contacts.

6. An electrode lead as claimed in claim 4, wherein
the relatively narrow contacts comprise coil contacts.

7. An electrode lead as claimed in claim 1, further comprising:
a wire, connected to the coil contact, that extends to the proximal end of the lead body.

8. An electrode lead as claimed in claim 1, wherein
the electrically conductive coils comprise helical coils.

9. An electrode lead as claimed in claim 1, wherein
the electrically conductive coils each define a central axis; and
the front outer surface of the cuff body and each of the central axes lie in a common plane.

10. An electrode lead as claimed in claim 1, wherein
the electrically conductive coils each define a central axis; and
each of the central axes are parallel to the front outer surface of the cuff body.

11. An electrode lead, comprising:
an elongate lead body having a proximal end and a distal end; and
a nerve paddle including
a biologically compatible, elastic, electrically insulative paddle body affixed to the distal end of the lead body, the contact body including front and rear outer surfaces, and defining a length, a length direction, a width, and a width direction, and
at least one electrically conductive coil partially embedded in the paddle body such that there are non-embedded portions, which together define a coil contact that is associated with the front outer surface, and embedded portions.

12. An electrode lead as claimed in claim 11, wherein
the at least one electrically conductive coil comprises a plurality of electrically conductive coils that are partially embedded in the paddle body such that each coil has non-embedded portions and embedded portions; and
a plurality of coil contacts that are associated with the front outer surface and are respectively defined by the non-embedded portions of each electrically conductive coil.

13. An electrode lead as claimed in claim 12, wherein
each of the electrically conductive coils defines a central axis having a shape; and
at least two of the plurality of electrically conductive coils have differently shaped central axes.

14. An electrode lead as claimed in claim 12, wherein
at least two of the coil contacts are relatively wide coil contacts that are separated from one another in the length direction; and
the electrode lead further comprises a plurality of relatively narrow contacts that are located between the relatively wide coil contacts.

15. An electrode lead as claimed in claim 14, wherein
the relatively narrow contacts comprise coil contacts.

16. An electrode lead as claimed in claim 11, wherein
the non-embedded portions of the at least one electrically conductive coil project outwardly from the front outer surface of the paddle body.

17. An electrode lead as claimed in claim 11, wherein
the at least one electrically conductive coil defines a central axis having a shape selected from the group consisting of a spiral shape, an m-shape, a wave-like shape, and a closed geometric shape.

18. An electrode lead as claimed in claim 11, wherein
the at least one electrically conductive coil comprises a helical coil.

19. An electrode lead as claimed in claim 11, wherein
the at least one electrically conductive coil defines a central axis; and
the central axis and the front outer surface of the paddle body lie in a common plane.

\* \* \* \* \*